(12) United States Patent
Gray

(10) Patent No.: US 8,480,715 B2
(45) Date of Patent: Jul. 9, 2013

(54) SPINAL IMPLANT SYSTEM AND METHOD

(75) Inventor: Wayne Gray, Pflugerville, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 1228 days.

(21) Appl. No.: 11/752,200

(22) Filed: May 22, 2007

(65) Prior Publication Data

US 2008/0294260 A1 Nov. 27, 2008

(51) Int. Cl.
*A61B 17/88* (2006.01)
*A61F 2/44* (2006.01)

(52) U.S. Cl.
USPC ........................................ 606/279; 623/17.16

(58) Field of Classification Search
USPC 606/281–282, 90, 99, 279; 623/17.11–17.16, 623/911
See application file for complete search history.

(56) References Cited

U.S. PATENT DOCUMENTS

| | | |
|---|---|---|
| 3,486,505 A | 12/1969 | Morrison |
| 4,143,332 A | 3/1979 | Michon et al. |
| 4,388,921 A | 6/1983 | Sutter et al. |
| 4,401,112 A | 8/1983 | Rezaian |
| 4,433,677 A | 2/1984 | Ulrich et al. |
| 4,492,226 A | 1/1985 | Belykh et al. |
| 4,501,269 A | 2/1985 | Bagby |
| 4,503,848 A | 3/1985 | Caspar et al. |
| 4,570,618 A | 2/1986 | Wu |
| 4,599,086 A * | 7/1986 | Doty ........................... 606/86 A |
| 4,604,995 A | 8/1986 | Stephens et al. |
| 4,641,636 A | 2/1987 | Cotrel |
| 4,643,178 A | 2/1987 | Nastari et al. |
| 4,697,586 A | 10/1987 | Gazale |
| 4,714,469 A | 12/1987 | Kenna |
| 4,743,256 A | 5/1988 | Brantigan |

(Continued)

FOREIGN PATENT DOCUMENTS

| | | |
|---|---|---|
| DE | 4323956 C1 | 10/1994 |
| EP | 0260044 B1 | 3/1988 |

(Continued)

OTHER PUBLICATIONS

International Search Report and Written Opinion mailed on Nov. 5, 2008 for International Application No. PCT/US2008/061933 (17 pp.).

(Continued)

*Primary Examiner* — Nicholas Woodall
*Assistant Examiner* — Larry E Waggle, Jr.
(74) *Attorney, Agent, or Firm* — Seager, Tufte & Wickhem, LLC

(57) ABSTRACT

Embodiments of the present invention provide a spinal implant system and method. One embodiment of the present invention includes a spinal implant comprising, a first implant plate, a second implant plate, a spacer member coupled between the first implant plate and the second implant plate and an end plate coupled to the spacer member, the end plate configured to couple to adjacent vertebrae. The implant plates can include spacer channels that receive the spacer member and insertion tool channels that receive an insertion tool. Preferably, on each implant plate, the spacer channel is near the center of the plate and the insertion tool channels are on either side of the spacer channel. The spacer channels and insertion tool channels can be dovetailed or otherwise shaped to capture a portion of the spacer member and insertion tool. Mating connectors can prevent removal of the spacer member from the spacer channels.

17 Claims, 22 Drawing Sheets

U.S. PATENT DOCUMENTS

| | | |
|---|---|---|
| 4,763,644 A | 8/1988 | Webb |
| 4,768,787 A | 9/1988 | Shira |
| 4,805,602 A | 2/1989 | Puno et al. |
| 4,834,757 A | 5/1989 | Brantigan |
| 4,863,476 A | 9/1989 | Shepperd |
| 4,878,915 A | 11/1989 | Brantigan |
| 4,887,596 A | 12/1989 | Sherman |
| 4,946,458 A | 8/1990 | Harms et al. |
| 4,950,269 A | 8/1990 | Gaines |
| 4,961,740 A | 10/1990 | Ray et al. |
| 4,964,641 A | 10/1990 | Miesch et al. |
| 4,966,600 A | 10/1990 | Songer et al. |
| 4,987,892 A | 1/1991 | Krag et al. |
| 5,005,562 A | 4/1991 | Cotrel |
| 5,026,373 A | 6/1991 | Ray et al. |
| 5,047,029 A | 9/1991 | Aebi et al. |
| 5,055,104 A | 10/1991 | Ray |
| 5,074,864 A | 12/1991 | Cozad et al. |
| 5,102,412 A | 4/1992 | Rogozinski |
| 5,108,399 A | 4/1992 | Eitenmuller et al. |
| 5,108,446 A | 4/1992 | Wagner et al. |
| 5,116,340 A | 5/1992 | Songer et al. |
| 5,123,926 A | 6/1992 | Pisharodi |
| 5,127,912 A | 7/1992 | Ray et al. |
| 5,129,388 A | 7/1992 | Vignaud et al. |
| 5,129,904 A | 7/1992 | Illi |
| 5,147,359 A | 9/1992 | Cozad et al. |
| 5,154,718 A | 10/1992 | Cozad et al. |
| 5,171,278 A | 12/1992 | Pisharodi |
| 5,176,678 A | 1/1993 | Tsou |
| 5,176,680 A | 1/1993 | Vignaud et al. |
| 5,181,917 A | 1/1993 | Rogozinski |
| 5,192,321 A | 3/1993 | Strokon |
| 5,192,327 A | 3/1993 | Brantigan |
| 5,201,734 A | 4/1993 | Cozad et al. |
| 5,242,445 A | 9/1993 | Ashman |
| 5,242,448 A | 9/1993 | Pettine et al. |
| 5,246,442 A | 9/1993 | Ashman et al. |
| 5,261,909 A | 11/1993 | Sutterlin et al. |
| 5,263,953 A | 11/1993 | Bagby |
| 5,281,222 A | 1/1994 | Allard et al. |
| 5,282,801 A | 2/1994 | Sherman |
| 5,290,312 A | 3/1994 | Kojimoto et al. |
| 5,290,494 A | 3/1994 | Coombes et al. |
| 5,303,718 A | 4/1994 | Krajicek |
| 5,304,179 A | 4/1994 | Wagner |
| 5,306,307 A | 4/1994 | Senter et al. |
| 5,306,309 A | 4/1994 | Wagner et al. |
| 5,312,405 A | 5/1994 | Korotko et al. |
| 5,312,410 A | 5/1994 | Miller et al. |
| 5,318,566 A | 6/1994 | Miller |
| 5,336,223 A | 8/1994 | Rogers |
| 5,336,240 A | 8/1994 | Metzler et al. |
| 5,344,422 A | 9/1994 | Frigg |
| 5,348,026 A | 9/1994 | Davidson |
| 5,357,983 A | 10/1994 | Matthews |
| 5,360,429 A | 11/1994 | Jeanson et al. |
| 5,360,431 A | 11/1994 | Puno et al. |
| 5,361,766 A | 11/1994 | Nichols et al. |
| 5,364,399 A | 11/1994 | Lowery et al. |
| 5,370,697 A | 12/1994 | Baumgartner |
| 5,380,325 A | 1/1995 | Lahille et al. |
| 5,385,583 A | 1/1995 | Cotrel |
| 5,390,683 A | 2/1995 | Pisharodi |
| 5,395,374 A | 3/1995 | Miller et al. |
| 5,397,364 A | 3/1995 | Kozak et al. |
| 5,403,315 A | 4/1995 | Ashman |
| 5,405,391 A | 4/1995 | Hednerson et al. |
| 5,415,658 A | 5/1995 | Kilpela et al. |
| 5,417,690 A | 5/1995 | Sennett et al. |
| 5,423,820 A | 6/1995 | Miller et al. |
| 5,423,825 A | 6/1995 | Levine |
| 5,425,772 A | 6/1995 | Brantigan |
| 5,429,863 A | 7/1995 | McMillin |
| 5,431,658 A | 7/1995 | Moskovich |
| 5,443,514 A | 8/1995 | Steffee |
| 5,458,642 A | 10/1995 | Beer et al. |
| 5,466,237 A | 11/1995 | Byrd, III et al. |
| 5,474,555 A | 12/1995 | Puno et al. |
| 5,480,437 A | 1/1996 | Draenert |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland et al. |
| 5,505,732 A | 4/1996 | Michelson |
| 5,507,746 A | 4/1996 | Lin |
| 5,514,180 A | 5/1996 | Heggeness et al. |
| 5,520,690 A | 5/1996 | Errico et al. |
| 5,522,899 A | 6/1996 | Michelson |
| 5,526,664 A | 6/1996 | Vetter |
| 5,527,341 A | 6/1996 | Gogolewski et al. |
| 5,531,746 A | 7/1996 | Errico et al. |
| 5,531,751 A | 7/1996 | Schultheiss et al. |
| 5,536,270 A | 7/1996 | Songer et al. |
| 5,536,271 A | 7/1996 | Daly et al. |
| 5,545,165 A | 8/1996 | Biedermann et al. |
| 5,549,608 A | 8/1996 | Errico et al. |
| 5,549,612 A | 8/1996 | Yapp et al. |
| 5,554,157 A | 9/1996 | Errico et al. |
| 5,554,191 A | 9/1996 | Lahille et al. |
| 5,563,124 A | 10/1996 | Damien et al. |
| 5,569,248 A | 10/1996 | Matthews |
| 5,569,253 A | 10/1996 | Farris et al. |
| 5,571,192 A | 11/1996 | Schonhoffer |
| 5,575,792 A | 11/1996 | Errico et al. |
| 5,578,033 A | 11/1996 | Errico et al. |
| 5,578,034 A | 11/1996 | Estes |
| 5,584,834 A | 12/1996 | Errico et al. |
| 5,586,984 A | 12/1996 | Errico et al. |
| 5,591,235 A | 1/1997 | Kuslich |
| 5,593,409 A | 1/1997 | Michelson |
| 5,601,553 A | 2/1997 | Trebing et al. |
| 5,601,556 A | 2/1997 | Pisharodi |
| 5,603,713 A | 2/1997 | Aust et al. |
| 5,607,424 A | 3/1997 | Tropiano |
| 5,607,425 A | 3/1997 | Rogozinski |
| 5,607,426 A | 3/1997 | Ralph et al. |
| 5,607,428 A | 3/1997 | Lin |
| 5,607,430 A | 3/1997 | Bailey |
| 5,609,592 A | 3/1997 | Brumfield et al. |
| 5,609,593 A | 3/1997 | Errico et al. |
| 5,609,594 A | 3/1997 | Errico et al. |
| 5,609,596 A | 3/1997 | Pepper |
| 5,609,635 A | 3/1997 | Michelson |
| 5,609,636 A | 3/1997 | Kohrs et al. |
| 5,611,800 A | 3/1997 | Davis et al. |
| 5,611,801 A | 3/1997 | Songer |
| 5,613,967 A | 3/1997 | Engelhardt et al. |
| 5,616,144 A | 4/1997 | Yapp et al. |
| 5,620,443 A | 4/1997 | Gertzbein et al. |
| 5,624,441 A | 4/1997 | Sherman et al. |
| 5,626,579 A | 5/1997 | Muschler et al. |
| 5,628,740 A | 5/1997 | Mullane |
| 5,628,756 A | 5/1997 | Barker, Jr. et al. |
| 5,630,816 A | 5/1997 | Kambin |
| 5,632,747 A | 5/1997 | Scarborough et al. |
| 5,634,925 A | 6/1997 | Urbanski |
| 5,643,260 A | 7/1997 | Doherty |
| 5,643,264 A | 7/1997 | Sherman et al. |
| 5,643,265 A | 7/1997 | Errico et al. |
| 5,645,084 A | 7/1997 | McKay |
| 5,645,544 A | 7/1997 | Tai et al. |
| 5,645,549 A | 7/1997 | Boyd et al. |
| 5,645,598 A | 7/1997 | Brosnahan, III |
| 5,647,873 A | 7/1997 | Errico et al. |
| 5,649,927 A | 7/1997 | Kilpela et al. |
| 5,651,283 A | 7/1997 | Runciman et al. |
| 5,651,789 A | 7/1997 | Cotrel |
| 5,653,708 A | 8/1997 | Howland |
| 5,653,709 A | 8/1997 | Frigg |
| 5,653,763 A | 8/1997 | Errico et al. |
| 5,658,289 A | 8/1997 | Boucher et al. |
| 5,658,335 A | 8/1997 | Allen |
| 5,658,337 A | 8/1997 | Kohrs et al. |
| 5,658,516 A | 8/1997 | Eppley et al. |
| 5,662,653 A | 9/1997 | Songer et al. |
| 5,665,088 A | 9/1997 | Gil et al. |

| Patent No. | Date | Inventor(s) |
|---|---|---|
| 5,665,112 A | 9/1997 | Thal |
| 5,665,122 A | 9/1997 | Kambin |
| 5,667,506 A | 9/1997 | Sutterlin |
| 5,667,507 A | 9/1997 | Corin et al. |
| 5,667,508 A | 9/1997 | Errico et al. |
| 5,668,288 A | 9/1997 | Storey et al. |
| 5,669,909 A | 9/1997 | Zdeblick et al. |
| 5,669,910 A | 9/1997 | Korhonen et al. |
| 5,669,911 A | 9/1997 | Errico et al. |
| 5,671,695 A | 9/1997 | Schroeder |
| 5,672,175 A | 9/1997 | Martin |
| 5,672,176 A | 9/1997 | Biedermann et al. |
| 5,674,222 A | 10/1997 | Berger et al. |
| 5,674,295 A | 10/1997 | Ray et al. |
| 5,674,296 A | 10/1997 | Bryan et al. |
| 5,676,665 A | 10/1997 | Bryan |
| 5,676,666 A | 10/1997 | Oxland et al. |
| 5,676,701 A | 10/1997 | Yuan et al. |
| 5,676,703 A | 10/1997 | Gelbard |
| 5,681,311 A | 10/1997 | Foley et al. |
| 5,681,312 A | 10/1997 | Yuan et al. |
| 5,683,391 A | 11/1997 | Boyd |
| 5,683,392 A | 11/1997 | Richelsoph et al. |
| 5,683,393 A | 11/1997 | Ralph |
| 5,683,394 A | 11/1997 | Rinner |
| 5,688,272 A | 11/1997 | Montague et al. |
| 5,688,273 A | 11/1997 | Errico et al. |
| 5,688,274 A | 11/1997 | Errico et al. |
| 5,688,279 A | 11/1997 | McNulty et al. |
| 5,688,280 A | 11/1997 | Booth, Jr. et al. |
| 5,690,629 A | 11/1997 | Asher et al. |
| 5,690,630 A | 11/1997 | Errico et al. |
| 5,690,631 A | 11/1997 | Duncan et al. |
| 5,690,632 A | 11/1997 | Schwartz et al. |
| 5,690,633 A | 11/1997 | Taylor et al. |
| 5,690,842 A | 11/1997 | Panchison |
| 5,693,046 A | 12/1997 | Songer et al. |
| 5,693,053 A | 12/1997 | Estes |
| 5,693,100 A | 12/1997 | Pisharodi |
| 5,697,929 A | 12/1997 | Mellinger |
| 5,697,977 A | 12/1997 | Pisharodi |
| 5,700,291 A | 12/1997 | Kuslich et al. |
| 5,700,292 A | 12/1997 | Margulies |
| 5,702,391 A | 12/1997 | Lin |
| 5,702,392 A | 12/1997 | Wu et al. |
| 5,702,393 A | 12/1997 | Pfaifer |
| 5,702,394 A | 12/1997 | Henry et al. |
| 5,702,395 A | 12/1997 | Hopf |
| 5,702,396 A | 12/1997 | Hoenig et al. |
| 5,702,399 A | 12/1997 | Kilpela et al. |
| 5,702,449 A | 12/1997 | McKay |
| 5,702,450 A | 12/1997 | Bisserie |
| 5,702,451 A | 12/1997 | Biedermann et al. |
| 5,702,452 A | 12/1997 | Argenson et al. |
| 5,702,453 A | 12/1997 | Rabbe et al. |
| 5,702,454 A | 12/1997 | Baumgartner |
| 5,702,455 A | 12/1997 | Saggar |
| 5,704,936 A | 1/1998 | Mazel |
| 5,704,937 A | 1/1998 | Martin |
| 5,707,372 A | 1/1998 | Errico et al. |
| 5,707,395 A | 1/1998 | Li |
| 5,709,681 A | 1/1998 | Pennig |
| 5,709,682 A | 1/1998 | Medoff |
| 5,709,683 A | 1/1998 | Bagby |
| 5,709,684 A | 1/1998 | Errico et al. |
| 5,709,685 A | 1/1998 | Dombrowski et al. |
| 5,709,686 A | 1/1998 | Talos et al. |
| 5,713,841 A | 2/1998 | Graham |
| 5,713,898 A | 2/1998 | Stucker et al. |
| 5,713,899 A | 2/1998 | Marnay et al. |
| 5,713,900 A | 2/1998 | Benzel et al. |
| 5,713,903 A | 2/1998 | Sander et al. |
| 5,713,904 A | 2/1998 | Errico et al. |
| 5,716,355 A | 2/1998 | Jackson |
| 5,716,356 A | 2/1998 | Biedermann et al. |
| 5,716,357 A | 2/1998 | Rogozinski |
| 5,716,358 A | 2/1998 | Ochoa et al. |
| 5,716,359 A | 2/1998 | Ojima et al. |
| 5,716,415 A | 2/1998 | Steffee |
| 5,716,416 A | 2/1998 | Lin |
| 5,720,746 A | 2/1998 | Soubeiran |
| 5,720,747 A | 2/1998 | Burke |
| 5,720,748 A | 2/1998 | Kuslich et al. |
| 5,720,751 A | 2/1998 | Jackson |
| 5,722,977 A | 3/1998 | Wilhelmy |
| 5,749,916 A | 5/1998 | Richelsoph |
| 5,776,199 A | 7/1998 | Michelson |
| 5,782,830 A | 7/1998 | Farris |
| 5,782,832 A | 7/1998 | Larsen et al. |
| 5,782,919 A | 7/1998 | Zdeblick et al. |
| 5,785,710 A | 7/1998 | Michelson |
| 5,797,909 A | 8/1998 | Michelson |
| 5,800,550 A | 9/1998 | Sertich |
| 5,814,084 A | 9/1998 | Grivas et al. |
| 5,860,973 A | 1/1999 | Michelson |
| 5,865,847 A | 2/1999 | Kohrs et al. |
| 5,876,457 A | 3/1999 | Picha et al. |
| 5,888,223 A | 3/1999 | Bray, Jr. |
| 5,888,227 A | 3/1999 | Cottle |
| 5,895,427 A | 4/1999 | Kuslich et al. |
| 5,897,556 A | 4/1999 | Drewry et al. |
| 5,897,593 A | 4/1999 | Kohrs et al. |
| 5,916,267 A * | 6/1999 | Tienboon ............... 623/17.11 |
| 5,947,971 A | 9/1999 | Kuslich et al. |
| 5,961,554 A | 10/1999 | Janson et al. |
| 5,980,522 A | 11/1999 | Koros et al. |
| 5,984,922 A | 11/1999 | McKay |
| 6,030,635 A | 2/2000 | Gertzman et al. |
| 6,033,438 A | 3/2000 | Bianchi et al. |
| 6,045,579 A | 4/2000 | Hochshuler et al. |
| 6,080,193 A | 6/2000 | Hochshuler et al. |
| 6,083,225 A | 7/2000 | Winslow et al. |
| 6,090,143 A | 7/2000 | Meriwether et al. |
| 6,096,044 A | 8/2000 | Boyd et al. |
| 6,099,527 A | 8/2000 | Hochschuler et al. |
| 6,106,557 A | 8/2000 | Robioneck et al. |
| 6,113,602 A | 9/2000 | Sand |
| 6,113,638 A | 9/2000 | Williams et al. |
| 6,123,705 A | 9/2000 | Michelson |
| 6,139,551 A | 10/2000 | Michelson et al. |
| 6,146,420 A | 11/2000 | McKay |
| 6,149,651 A | 11/2000 | Drewry et al. |
| 6,156,037 A | 12/2000 | LeHuec |
| 6,174,311 B1 | 1/2001 | Branch et al. |
| 6,176,882 B1 | 1/2001 | Biedermann et al. |
| 6,183,517 B1 | 2/2001 | Suddaby |
| 6,190,414 B1 | 2/2001 | Young et al. |
| 6,193,757 B1 | 2/2001 | Foley et al. |
| 6,197,033 B1 | 3/2001 | Haid, Jr. et al. |
| 6,200,322 B1 | 3/2001 | Branch et al. |
| 6,206,922 B1 | 3/2001 | Zdeblick et al. |
| 6,210,412 B1 | 4/2001 | Michelson |
| 6,224,595 B1 | 5/2001 | Michelson |
| 6,224,607 B1 | 5/2001 | Michelson |
| 6,224,631 B1 | 5/2001 | Kohrs |
| 6,235,059 B1 | 5/2001 | Benezech et al. |
| 6,241,729 B1 | 6/2001 | Estes et al. |
| 6,241,770 B1 | 6/2001 | Michelson |
| 6,245,072 B1 | 6/2001 | Zdeblick et al. |
| 6,245,108 B1 | 6/2001 | Biscup |
| 6,251,140 B1 | 6/2001 | Marino et al. |
| 6,261,296 B1 | 7/2001 | Aebi et al. |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Houfburg |
| 6,287,343 B1 | 9/2001 | Kuslich et al. |
| 6,290,724 B1 | 9/2001 | Marino |
| 6,296,665 B1 | 10/2001 | Strnad et al. |
| 6,302,914 B1 | 10/2001 | Michelson |
| 6,309,421 B1 | 10/2001 | Pisharodi |
| 6,325,827 B1 | 12/2001 | Lin |
| 6,342,074 B1 | 1/2002 | Simpson |
| 6,346,122 B1 | 2/2002 | Picha et al. |
| 6,371,986 B1 | 4/2002 | Bagby |
| 6,371,989 B1 | 4/2002 | Chauvin et al. |
| 6,375,655 B1 | 4/2002 | Zdeblick et al. |
| 6,387,130 B1 | 5/2002 | Stone et al. |

| | | | |
|---|---|---|---|
| 6,395,030 B1 * | 5/2002 | Songer et al. | 623/17.11 |
| 6,409,766 B1 | 6/2002 | Brett | |
| 6,416,515 B1 | 7/2002 | Wagner | |
| 6,419,705 B1 | 7/2002 | Erickson | |
| 6,423,095 B1 | 7/2002 | Van Hoeck et al. | |
| 6,428,541 B1 | 8/2002 | Boyd et al. | |
| 6,432,106 B1 | 8/2002 | Fraser | |
| 6,432,107 B1 | 8/2002 | Ferree | |
| 6,436,098 B1 | 8/2002 | Michelson | |
| 6,447,544 B1 | 9/2002 | Michelson | |
| 6,447,545 B1 | 9/2002 | Bagby | |
| 6,447,547 B1 | 9/2002 | Michelson | |
| 6,454,806 B1 | 9/2002 | Cohen et al. | |
| 6,458,159 B1 | 10/2002 | Thalgott | |
| 6,461,359 B1 | 10/2002 | Tribus et al. | |
| 6,468,276 B1 | 10/2002 | McKay | |
| 6,471,724 B2 | 10/2002 | Zdeblick et al. | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,724 B1 | 12/2002 | Ferree | |
| 6,500,205 B1 | 12/2002 | Michelson | |
| 6,517,544 B1 | 2/2003 | Michelson | |
| 6,520,967 B1 | 2/2003 | Cauthen | |
| 6,520,993 B2 | 2/2003 | James et al. | |
| 6,524,318 B1 | 2/2003 | Longhini et al. | |
| 6,562,074 B2 | 5/2003 | Gerbec et al. | |
| 6,576,016 B1 | 6/2003 | Hochshuler et al. | |
| 6,576,017 B2 | 6/2003 | Foley et al. | |
| 6,610,093 B1 | 8/2003 | Pisharodi | |
| 6,641,614 B1 | 11/2003 | Wagner et al. | |
| 6,648,917 B2 | 11/2003 | Gerbec et al. | |
| 6,652,533 B2 | 11/2003 | O'Neil | |
| 6,706,070 B1 | 3/2004 | Wagner et al. | |
| 6,716,218 B2 | 4/2004 | Holmes et al. | |
| 6,726,720 B2 * | 4/2004 | Ross et al. | 623/17.13 |
| 6,764,491 B2 | 7/2004 | Frey et al. | |
| 6,852,129 B2 | 2/2005 | Gerbec et al. | |
| 6,893,464 B2 | 5/2005 | Kiester | |
| 6,899,735 B2 * | 5/2005 | Coates et al. | 623/17.16 |
| 7,001,432 B2 * | 2/2006 | Keller et al. | 623/17.14 |
| 7,060,097 B2 * | 6/2006 | Fraser et al. | 623/17.11 |
| 7,112,222 B2 | 9/2006 | Fraser et al. | |
| 7,118,580 B1 * | 10/2006 | Beyersdorff et al. | 606/99 |
| 7,419,505 B2 * | 9/2008 | Fleischmann et al. | 623/17.11 |
| 7,625,379 B2 * | 12/2009 | Puno et al. | 606/99 |
| 2001/0020185 A1 | 9/2001 | Ray | |
| 2002/0058939 A1 * | 5/2002 | Wagner et al. | 606/61 |
| 2002/0169508 A1 * | 11/2002 | Songer et al. | 623/17.11 |
| 2004/0002761 A1 * | 1/2004 | Rogers et al. | 623/17.13 |
| 2004/0030387 A1 * | 2/2004 | Landry et al. | 623/16.11 |
| 2004/0143332 A1 * | 7/2004 | Krueger et al. | 623/17.14 |
| 2004/0220590 A1 * | 11/2004 | Zubok et al. | 606/142 |
| 2004/0249377 A1 | 12/2004 | Kaes et al. | |
| 2005/0101960 A1 * | 5/2005 | Fiere et al. | 606/72 |
| 2005/0159813 A1 | 7/2005 | Molz | |
| 2006/0064107 A1 * | 3/2006 | Bertagnoli et al. | 606/99 |
| 2006/0235409 A1 | 10/2006 | Blain | |
| 2006/0235533 A1 | 10/2006 | Blain | |

FOREIGN PATENT DOCUMENTS

| | | |
|---|---|---|
| EP | 0578320 B1 | 1/1994 |
| EP | 0778007 A1 | 6/1997 |
| FR | 2717068 A1 | 9/1995 |
| FR | 2727005 | 5/1996 |
| FR | 2732887 A1 | 10/1996 |
| FR | 2736535 A1 | 1/1997 |
| FR | 2737656 A1 * | 2/1997 |
| FR | 2815846 | 5/2002 |
| JP | 2001190579 A2 | 7/2001 |
| SU | 1424826 A1 | 9/1988 |
| WO | WO 88/03781 A1 | 6/1988 |
| WO | WO 97/00054 A1 | 1/1997 |
| WO | WO 97/06753 A2 | 2/1997 |
| WO | WO 98/14142 A1 | 4/1998 |
| WO | WO 01/19295 A1 | 3/2001 |
| WO | WO 03/032812 A2 | 4/2003 |
| WO | WO 2004/054477 A1 | 7/2004 |
| WO | WO 2004/069106 | 8/2004 |

OTHER PUBLICATIONS

International Preliminary Report on Patentability for PCT/US2008/061933, issued Nov. 24, 2009, mailed Dec. 3, 2009, 11 pgs.
Examination Report issued for European Patent Application No. 08 747 133.0, mailed Nov. 8, 2010, 4 pgs.
Danek Group, Inc., Medical Divisional Publication entitled "TSRH Spinal System—Unmatched versatility," pp. 1-4, 1992.
Danek Surgical Technique Manual entitled "TSRH Spinal Implant System," pp. 1-16.
Danek Surgical Technique Manual entitled "TSRH Crosslink," pp. 1-8.
Dickman, Curtis A., et al., BNI Quarterly Publication entitled "Techniques of Screw Fixation of the Cervical Spine," vol. 9 No. 4, pp. 27-39, Fall 1993.
Slone et al., RadioGraphics Publication entitled "Spinal Fixation," vol. 13 No. 2, pp. 341-356, Mar. 1993.
Synthes Spine Publication entitled "The Universal Spinal System—Internal Fixation to the Spine," pp. 1-15, 1994.
Acromed Publication entitled "The ISOLA Spinal System—Versatility, simplicity and minimal profile in the surgical treatment of the spine," pp. 1-15, 1994.
Danek Publication entitled "AXIS—Fixation System," pp. 1-6, 1993.
Synthes Publication entitled "Small Notched Titanium Reconstruction Plate System," pp. 1-6, 1996.
J. Neurosurg Publication entitled "Posterior plates in the management of cervical instability: long-term results in 44 patients," vol. 81, pp. 341-349, 1994.
BNI Quarterly Publication entitled "Lateral Mass Posterior Plating and Facet Fusion for Cervical Spine Instability," vol. 7, No. 2, pp. i,ii, 1-12, 1991.
Beadling, Lee, Orthopedics Today Publication entitled "FDA Clears Spinal Cages for Interbody Lumbar Fusion," pp. 1-2.
MedPro Month Publication entitled "Trends in Spine & Disk Surgery," vol. VI, No. 11-12, pp. 280-284.
Surgical Dynamics Ray Threaded Fusion Cage Device Surgical Technique Manual, pp. 1-10.
Surgical Dynamics Ray Threaded Fusion Cage, pp. 1-6.
AcroMed Publication entitled "AcroMed Spinal Solutions for Cervical Pathologies," pp. 1-8, Jul. 1995.
Codman Publication entitled "Sof'wire Cable System," 6 pp.
Huhn, Stephen L. et al., "Posterior Spinal Osteosynthesis for Cervical Fracture/Dislocation Using a Flexible Multistrand Cable System: Technical Note," Neurosurgery, vol. 29, No. 6, pp. 943-946, 1991.
Dickman, Curtis A. et al., "Wire Fixation for the Cervical Spine: Biomechanical Principles and Surgical Techniques," BNI Quarterly, vol. 9, No. 4, pp. 2-16, Fall 1993.
Publication by AcroMed entitled "ACROMED Cable System by Songer," 4 pp., Sep. 1993.
M. Aebi, M.D., et al., "Treatment of Cervical Spine Injuries with Anterior Plating: Indications, Techniques, and Results," vol. 16, No. 3S, pp. S38-S45, Mar. 1991 Supplement.
Foley, M.D., et al., "Aline Anterior Cervical Plating System," Smith & Nephew Richards, Inc., Orthopaedics Catalog Information, pp. 1-16, Sep. 1996.
Lowery, Gary L., M.D., Ph.D., Sofamor Danek Group, Inc. Publication entitled "Orion Anterior Cervical Plate System: Surgical Technique," pp. 1-24, 1994.
Apfelbaum, R., M.D., Aesculap Scientific Information publication entitled, "Posterior Transarticular C1-2 Screw Fixation for Atlantoaxial Instability," pp. 1-15, 1993.
Danek Titanium Cable System publication by Danek Group, Inc., 6 pp., 1994.
Publication entitled "Spinal Disorders," 4 pp.
O'Brien, John P., Ph.D., Orthopaedic Product News Article entitled "Interbody Fusion of the Lumbar Spine," pp. 1-3.
Roy et al., "Variation of Young's Modulus and Hardness in Human Lumbar Vertebrae Measured by Nanoindentation," pp. 1-4.
Sofamor Danek publication entitled "Atlas Cable System: Evolution of the Cable System for Spinal Applications," 2 pp., 1995.
AcroMed Corporation Publication entitled "The ISOLA Transverse Rod Connectors: Principles and Techniques," 10 pp.

Songer, Matthew, M.D., "Acromed Cable System by Songer: Cervical Technique Manual," pp. 1-17.

Songer, Matthew N., M.D., "Acromed Cable System by Songer: Technique Manual," pp. 1-20, 1993.

Oxland, Thomas R., Ph.D., et al., SpineTech Inc. Publication entitled "Biomechanical Rationale—The BAK Interbody Fusion System: An Innovative Solutions," pp. 1-16.

SpineTech, Inc. publication entitled "Patient Information on Spinal Fusion Surgery and the BAK Interbody Fusion System," 10 pp.

SpineTech, Inc., publication entitled "BAK/Cervical Interbody Fusion System," 2 pp., 1994.

SpineTech, Inc. publications entitled "Instrumentation BAK Interbody Fusion System," "Biomechanics BAK Interbody Fusion System," and "Porosity BAK Interbody Fusion System," 12 pp., 1996.

SpineTech, Inc. publication entitled "The BAK Interbody Fusion System," 4 pp., 1996.

Deputy Motech, Inc. publication entitled "Moss Miami 3-Dimensional Spinal Instrumentation: Taking Spinal Instrumentation to a New Dimension," 8 pp., 1995.

Shufflebarger, Harry L., M.D., "Moss Miama Spinal Instrumentation System: Methods of Fixation of the Spondylopelvic Junction," Lumbosacral and Spinopelvic Fixation, Raven Publishers, Philadelphia, pp. 381-393., 1996.

Shufflebarger, Harry L., M.D., Dupuy Motech publication entitled "Clinical Issue: Rod Rotation in Scoliosis Surgery," 5 pp.

AcroMed publication entitled, "Instruments," 3 pp.

SpineTech, Inc. publication entitled, "The Bone Harvester," 2pp., 1996.

Wright Medical Technology Publication entitled, "Versalok Low Back Fixation System," pp. 1-4, 1996.

Danek Medical, Inc. Publication entitled, "TSRH Lumbar System," pp. 1-4, 1991.

Spinal Concepts Inc. Publication entitled, "The BacFix ss—Posterior Lower Back Fixation System—Written Surgical Technique," pp. 1-11, 1997.

Dialog Web results for search for English language abstract for SU1424826 downloaded and printed from www.dialogweb.com on Jan. 22, 1999 (2 pages), Sep. 23, 1988.

Dialog Web results for search for English language abstract for DE 4323956 downloaded and printed from www.dialogweb.com on Jan. 22, 1999 (2 pages), Jul. 19, 1993.

Dialog Web results for search for English language abstract for fr2717068 downloaded and printed from www.dialogweb.com on Jan. 22, 1999 (1 page), Sep. 15, 1995.

* cited by examiner

SPINAL IMPLANT SYSTEM AND METHOD

TECHNICAL FIELD OF THE INVENTION

Embodiments of the present invention relate to spinal implants. Even more particularly, embodiments of the present invention relate to spinal implants that utilize implant plates and spacers.

BACKGROUND OF THE INVENTION

An intervertebral disc may be subject to degeneration due to trauma, disease, and/or aging. Treatment of a degenerated disc may include partial or full removal of the intervertebral disc. This may destabilize the spinal column resulting in subsidence or deformation of vertebrae and possible alteration of the natural separation distance between adjacent vertebrae. During spinal fixation surgery, a spinal implant can be inserted in the space created by the removal or partial removal of the intervertebral disc between adjacent vertebrae. The spinal implant may maintain the height of the spine and restore stability to the spine. Maintaining the appropriate distance between the vertebrae helps reduce the pressure applied to nerves that pass between the vertebral bodies, thereby reducing pain and nerve damage.

Various types of spinal implants may be inserted into the space provided by the discectomy. The spinal implant may be a fusion device that allows bone growth to fuse the implant to the adjacent vertebrae. One type of implant used to promote fusion includes a pair of engaging plates and struts. The engaging plates engage the vertebrae and the struts separate the engaging plates to provide the appropriate separation. The engaging plates can be selected to achieve a desired lordotic angle. Implants having engaging plates and struts are described in U.S. Pat. No. 6,045,579 by Hochschuer et al., U.S. Provisional Patent Application No. 60/363,219 by Landry et al. and U.S. patent application Ser. No. 10/387,361 by Landry et al., each of which is fully incorporated by reference herein.

Spinal implants as described above can provide the proper lordotic alignment and vertebral separation for a particular patient. Such implants, however, typically rely on the compressive forces of the spine to hold them in place. The spinal implant, however, may move laterally causing the implant to become misaligned.

SUMMARY OF THE INVENTION

Embodiments of the present invention provide a spinal implant system and method. One embodiment of the present invention includes a spinal implant comprising a first implant plate, a second implant plate, a spacer member coupled between the first implant plate and the second implant plate and an end plate coupled to the spacer member, the end plate configured to couple to adjacent vertebrae. The implant plates can include spacer channels that receive the spacer member and insertion tool channels that receive an insertion tool. Preferably, on each implant plate, the spacer channel is near the center of the plate and the insertion tool channels are on either side of the spacer channel. The spacer channels and insertion tool channels can be dovetailed or otherwise shaped to capture a portion of the spacer member and insertion tool. Mating connectors can prevent removal of the spacer member from the spacer channels.

The implant plates can have various sizes. Additionally, the implant plates can have various slopes to achieve a particular lordotic angle when implanted. The spacer member can also have a selected shape to achieve a desired separation between the implant plates and lordotic angle. According to one embodiment, the end plate and spacer member can be a single piece of material.

Another embodiment of the present invention can include a spinal implant comprising a first implant plate, a second implant plate, a spacer member at least partially inserted between the first implant plate and the second implant plate and an end plate integrated with the spacer member configured to couple to adjacent vertebrae. The first implant plate can include a first spacer channel, a first insertion tool channel and a second insertion tool channel. The first spacer channel can be least partially defined by sidewalls configured to capture at least a first portion of the spacer member. The first insertion tool channel and the second insertion tool channel are positioned on opposite sides of the first spacer channel and can be at least partially defined by sidewalls configured to capture respective portions of the insertion tool. The second implant plate can comprise a second spacer channel, third insertion tool channel and fourth insertion tool channel. The second spacer channel can be at least partially defined by sidewalls configured to capture at least a second portion of the spacer member. The third insertion tool channel and fourth insertion tool channel are positioned on opposite sides of the second spacer channel and can be at least partially defined by sidewalls configured to capture respective portions of the insertion tool.

Another embodiment of the present invention can include a method of forming a spinal implant comprising inserting a first implant plate having a first spacer channel and a second implant plate having a second spacer channel in a space between adjacent vertebrae, distracting the first implant plate and second implant plate from an initial position to a second position with an insertion tool, moving an end plate and spacer member to insert the spacer member in the first spacer channel and the second spacer channel, and fastening the end plate to the adjacent vertebrae. The spacer member is guided to the first spacer channel and second spacer channel using the insertion tool.

Yet another embodiment of the present invention can include a spreader for forming an implant between adjacent bone structures comprising, a first arm configured to couple to first implant plate and a second arm configured to couple to a second implant plate. The first arm and second arm are configured to distract to move the first implant plate and second implant from an initial position to a distracted position and are shaped to guide an end plate and spacer member from a first position to a second position in which the spacer member is coupled to the first implant plate and the second implant plate.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION OF THE INVENTION

Figure 1:
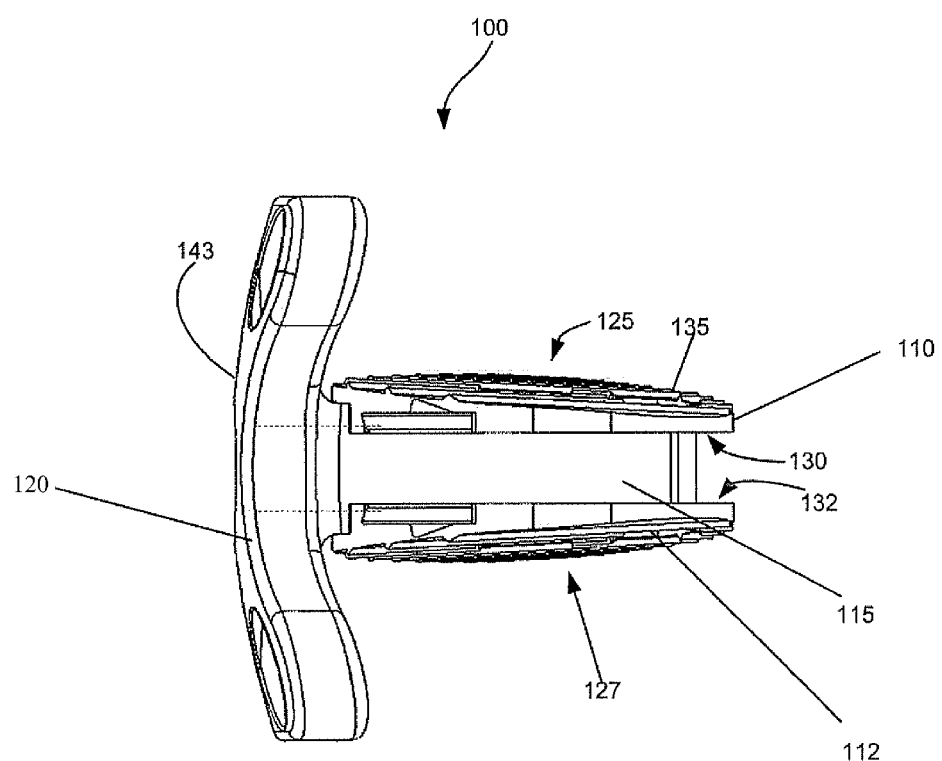
FIG. 1 is a diagrammatic representation of a side view of one embodiment of a spinal implant.

Preferred embodiments of the invention are illustrated in the FIGURES, like numerals being used to refer to like and corresponding parts of the various drawings.

Embodiments of the present invention provide spinal implants and methods. The spinal implant may be a fusion device that allows bone growth to fuse the implant to the adjacent vertebrae. According to one embodiment, a spinal implant can include implant plates to engage adjacent vertebrae and a spacer to maintain separation between the implant plates. The connection between the implant plates and spacer can be a frictional or interference connection that prevents the implant plates from fully disengaging from the spacer. According to one embodiment, for example, each engaging plate can include a dovetailed channel that receives a complementarily shaped portion of the spacer. The dovetails (or shaped surface) prevent the implant plates from vertically separating from the spacer during use. The friction and/or interference connection can limit relative motion of the spacer and implant plates to prevent the spacer and implant plates from disengaging. The spacer can be connected to or integrated with an end plate that attaches to the adjacent vertebral bodies using fasteners. The end plate can reduce stress on the spacer and prevent the spacer from exiting the space between the vertebral bodies. The spinal implant, according to one embodiment, can be adapted for anterior procedures such that a surgeon inserts the engaging plates from an anterior position and fastens the end plate to an anterior side of the vertebral bodies.

The implant plates can also be adapted to receive an insertion tool. Preferably, the insertion tool can be used to both separate the implant plates during insertion and guide the spacer to channels in the implant plate. According to one embodiment, the insertion tool can include two arms with one arm supporting the upper implant plate and the other arm supporting the lower implant plate. Each arm can include two or more prongs that are received by complementary channels in the respective implant plate. According to one embodiment, the prongs of the insertion tool are spaced so that they can straddle a portion of the end plate and act as guides to guide the end plate and the spacer to the implant plates. The end plate is positioned between the prongs so that the end plate can move towards the implant plates.

During a procedure, a surgeon can select the appropriate implant plates, spacer or end plate based on size, desired lordotic angle or other factors. The surgeon can position the end plate between the prongs of each arm of the insertion tool so that the end plate is unable to fall out of the insertion tool when prongs are parallel with the ground, but is able to move towards the end of the insertion tool. The surgeon can connect the implant plates to the end of each arm. The insertion tool can then be inserted into the body so that the engaging plates are in the cavity formed by the removal or partial removal of the vertebral disc. The surgeon can separate the arms of the insertion tool to distract the implant plates. When the implant plates are suitably positioned, the surgeon can move the end plate towards the implant plates causing the spacer to couple to the implant plates to complete the implant. The surgeon can further fasten the end plate to the vertebral bodies using suitable fasteners.

FIG. 1 is a diagrammatic representation of a side view one embodiment of an implant 100. Implant 100 can include implant plates 110 and 112 to contact the vertebrae, a spacer member 115 to maintain a vertical distance between the adjacent vertebrae and an end plate 120 to secure the implant. Spacer member 115 can be coupled to end plate 120 (e.g., as an integrated piece, using a fastener or through other suitable mechanism). Implant 100 can comprise any biocompatible material, including, but not limited to, titanium, titanium allow, stainless steel, ceramic material, bone, polymers or combinations thereof. In one embodiment, implant 100 is formed of a titanium and aluminum alloy, such as Ti6Al4V-Eli.

Implant plates 110 and 112 may have a variety of different form factors and sizes. For example, outer face 125 may be angled relative to inner face 130 and outer face 127 may be angled relative to inner face 132 so that a desired alignment of the adjacent vertebrae is achieved when implant 100 is in place. In other words, the outer faces of the implant plates may be sloped to allow an anterior side height to differ from a posterior side height. In another embodiment, spacer member 115 may be sloped to achieve a similar result. In addition to a slope, outer faces 125 and 127 may be curved. This curvature may allow outer faces 125 and 127 to substantially conform to the shapes of vertebral surfaces, particularly the anatomical domes of the respective vertebra. Preferably, outer faces 125 and 127 achieve at least 75% contact with the corresponding vertebrae.

Various surfaces of implant plates 110 and 112 can be treated to promote osseointegration. For example, outer faces 125 and 127 can be coated with titanium plasma spray, bone morphogenic proteins, hydroxyapatite and/or other coatings.

In addition to or instead of coating outer faces 125 and 127, outer faces 125 and 127 may be roughed by processes such as, but not limited to, chemical etching, surface abrading, shot peening, electric discharge roughening or embedding particles in the surface.

Implant plates 110 and 112 may include a number of protrusions 135 that can extend into adjacent vertebrae to better hold implant plates 110 and 112 in place. Protrusions 135 can be arranged in radial rows or other arrangements with any number of protrusions. Protrusions 135 can extend any distance, but preferably extend from 0.2 mm to 1 mm from the respective outer face.

Surgical kits for implant 100 can include any number of implant plates. For example, a surgical kit for implant 100 can include a number of small, medium and large implant plates with various slopes from that, as an example, range from 0 to 9 degrees in approximately three degree increments. This allows the surgeon to form implant 100 to have the appropriate sized plates for a patient and to achieve lordotic adjustment from about 0 degrees (where both implant plates have 0 degree slopes) to 18 degrees (where both implant plates have 9 degree slopes). In other embodiments, plates with different slopes can be selected (e.g., a lordotic adjustment of 9 degrees can be achieved by selecting an Implant plate with a 0 degree slope and an Implant plate with a 9 degree slope). In yet another embodiment, the surgeon can select spacer members and implant plates with various slopes to achieve the desired lordotic adjustment. The implant plates can be color coded and/or include other indicia to indicate size, slope and other parameters.

Implant plates 110 and 112 can couple to spacer member 115 using, for example, fasteners, chemical bonding, a friction fit, mating connectors or other suitable connection. In one embodiment, for example, a friction fit may be formed between spacer member 115 and implant plates 110 and 112 to couple implant plates 110 and 112 to spacer member 115. Channels that hold spacer member 115 may include projections that fit within indentions in spacer member 115 to form an interference fit when the spacer member 115 is fully inserted in the channel. Alternatively, the channels may include indentions that mate with projections extending from spacer member 115 when spacer member 115 is fully inserted into the channel of implant plates 110 and 112. In this case, implant plates 110 and 112 are held in place or limited in movement relative to spacer member 115 by both the friction fit and the mating connector. According to other embodiments, spacer member 115 or implant plates 110 and 112 may deform during attachment. A threshold amount of force may be required to connect implant plates 110 and 112 to spacer member 115 to inhibit unintentional full insertion of spacer member 115 into implant plates 110 and 112 and to inhibit removal of spacer member 115 once in place.

Spacer member 115 can be connected to or be integrated with plate 120. The size of spacer member 115 can be selected to provide the appropriate distance between implant plates 110 and 112 and hence the appropriate vertical distance between the vertebrae between which implant 100 is implanted. Spacer member 115 can also be shaped to limit the distance that implant plates 110 and 112 are inserted into the cavity between the vertebrae. Additionally, spacer member 115 can be shaped so that a desired lordotic angle is achieved when implant 100 is inserted. For example, spacer member 115 can include be a partial wedge shape with so that the anterior height of spacer member 115 is different than the posterior height of spacer member 115.

According to one embodiment, the center of spacer member 115 is a cavity (better shown in FIG. 7, discussed below). This cavity can be packed with bone growth material. By way of example, but not limitation, the bone growth material can include autograft bone (such as bone from the patient's lilac crest), allograft bone, synthetic bone growth material or combinations thereof.

End plate 120 can be flat, curved or have any suitable form factor for spinal surgery. Generally, end plate 120 includes holes for fasteners that allow plate 120 to be attached to the appropriate vertebrae. Examples of fasteners include, but are not limited to, bone screws, nails, rivets, trocars, pins, barbs or other threaded or non-threaded member which is securable within or to bone. According to one embodiment, bone screws can be attached to plate 120 in a manner that allows for polyaxial rotation prior to attachment to the bone. One example of a mechanism for attaching a plate to vertebrae that allows for polyaxial rotation of bone screws is described in U.S. patent application Ser. No. 10/036,012, entitled "System and Method for Stabilizing the Human Spine with a Bone Plate," by Wagner et al., filed Dec. 26, 2001, which is hereby fully incorporated by reference herein. End plate 120 may be attached to the spine with any number of fasteners.

End plate 120 and spacer member 115, according to one embodiment, can be formed of a single piece of material. End plate 120 can include a passage that opens to outer surface 143 of end plate 120 and the center of spacer member 115. The passage both strengthens end plate 120 under compressive loads and provides access to the center of spacer member 115.

Figure 2:
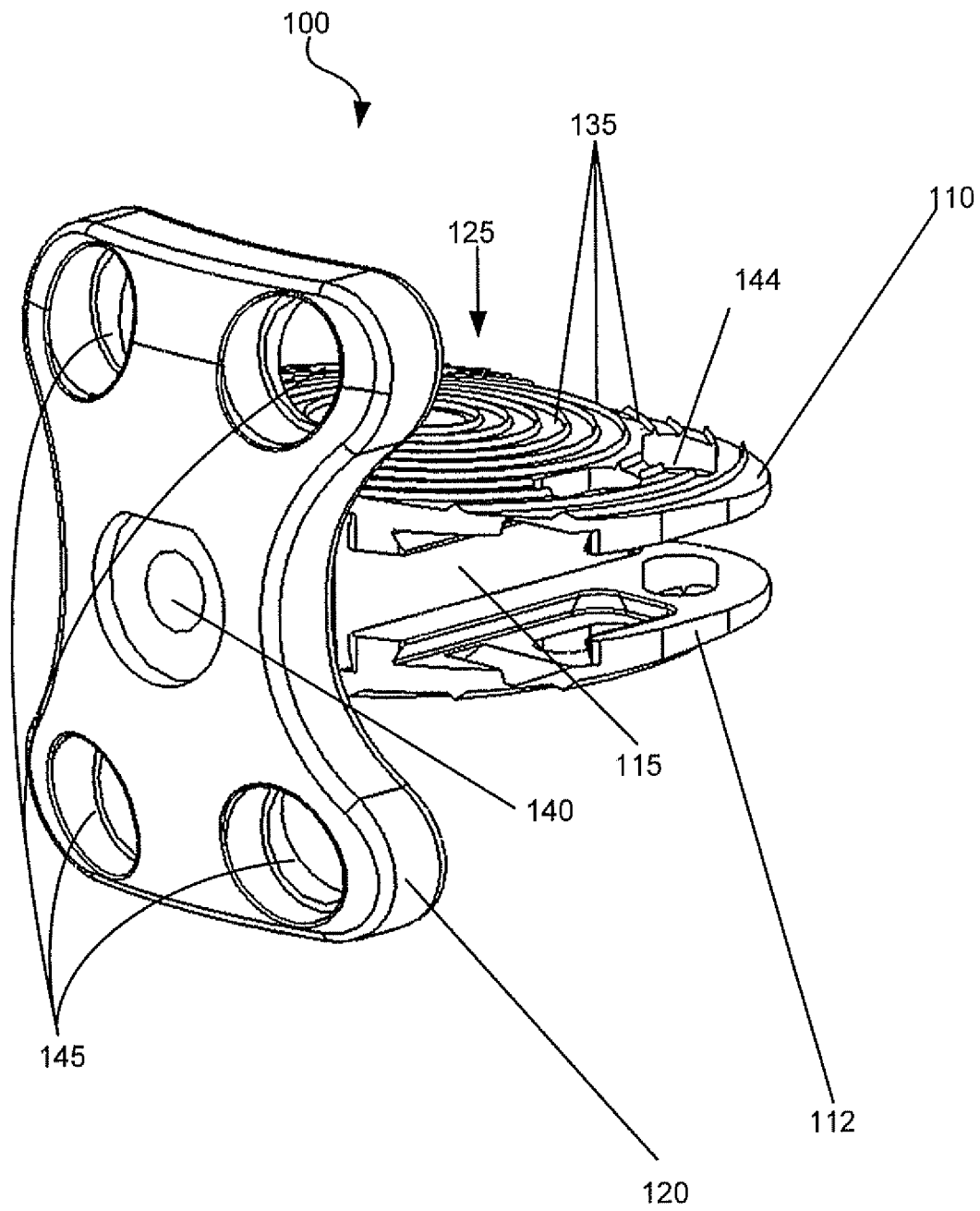
FIG. 2 is a diagrammatic representation of an oblique view of one embodiment of a spinal implant.

FIG. 2 is a diagrammatic representation illustrating an oblique view of one embodiment implant 100 showing end plate 120, spacer member 115 and implant plates 110 and 112, FIG. 2 emphasizes outer surface 125 of implant plate 110 and showing features such as protrusions 135 discussed above. Additionally, FIG. 2 illustrates an entrance to passage 140 that can lead to the cavity at the center of spacer member 115, FIG. 2 further illustrates that implant plates 110 and 112 can include holes defined there through (e.g., hole 144, for example). According to one embodiment, the holes of implant plate 110 can align with the holes of implant plate 112 when implant 100 is assembled. These holes can allow bone to pass as bone growth occurs, thereby allowing the vertebrae to fuse together. FIG. 2 further illustrates holes 145 for fasteners to attach plate 120 to the adjacent vertebrae.

Figure 3:
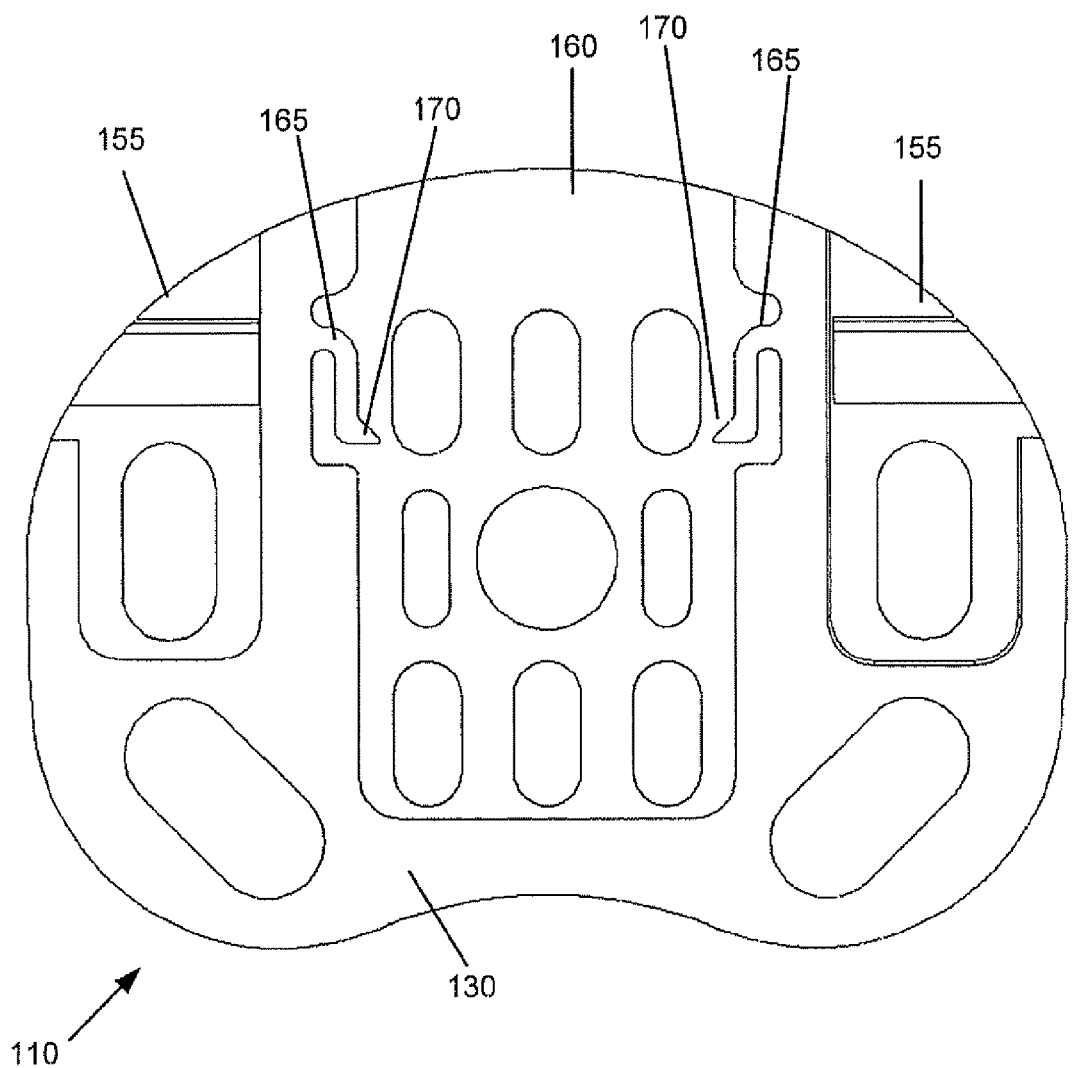
FIG. 3 is a diagrammatic representation of an inside surface of one embodiment of an implant plate.

FIG. 3 is a diagrammatic representation illustrating one embodiment of inner face 130 of implant plate 110. Inner face 130 can include recessed portions to define channels 155 and channel 160. According to one embodiment, channels 155 receive an insertion tool. The sidewalls of channels 155 can angled (e.g., dovetailed) or otherwise shaped to mate and form a frictional connection with the complementarily shaped insertion tool. Channels 155 and the complementary portion of the insertion tool can be shaped so that the insertion tool is only removed from implant plate 110 by sliding the insertion tool out of channels 155 in the opposite direction from which it was inserted into channels 155. The depth of insertion of the insertion tool can be limited by the length of channels 155, a stop in the channels, a stop on the insertion tool or by other mechanism.

Channel 160 can be shaped and sized to engage with spacer member 115. The sidewalls of channel 160 can also be angled (e.g., dovetailed) or otherwise shaped to capture spacer member 115. Implant plate 110 can include detents 165 with protrusions 170 that help prevent spacer member 115 from sliding out of channel 160. Detents 165 can be formed so that they return to approximately their original positions if pushed outward from the center of channel 160. As spacer member 115 slides into channel 160, detents 165 can push away from the center of channel 160 until protrusions 170 fit in complementary indentions in spacer member 115 (shown in FIG. 7). Protrusions 170 and the complementary indentions mate to limit movement of implant plate 110 (and implant 112) relative to spacer member 115. Preferably, movement is limited so that spacer member 115 can not be easily removed from implant plate 110. In other words, the mating connection (or other connection) prevents implant plate 110 from sliding off of spacer member 115 during expected use as a spinal implant. The depth of insertion of spacer member 115 can be limited by the length of channel 160, a stop in channel 160, a stop on spacer member 115 or end plate 120 or by other suitable mechanism.

Figure 4:
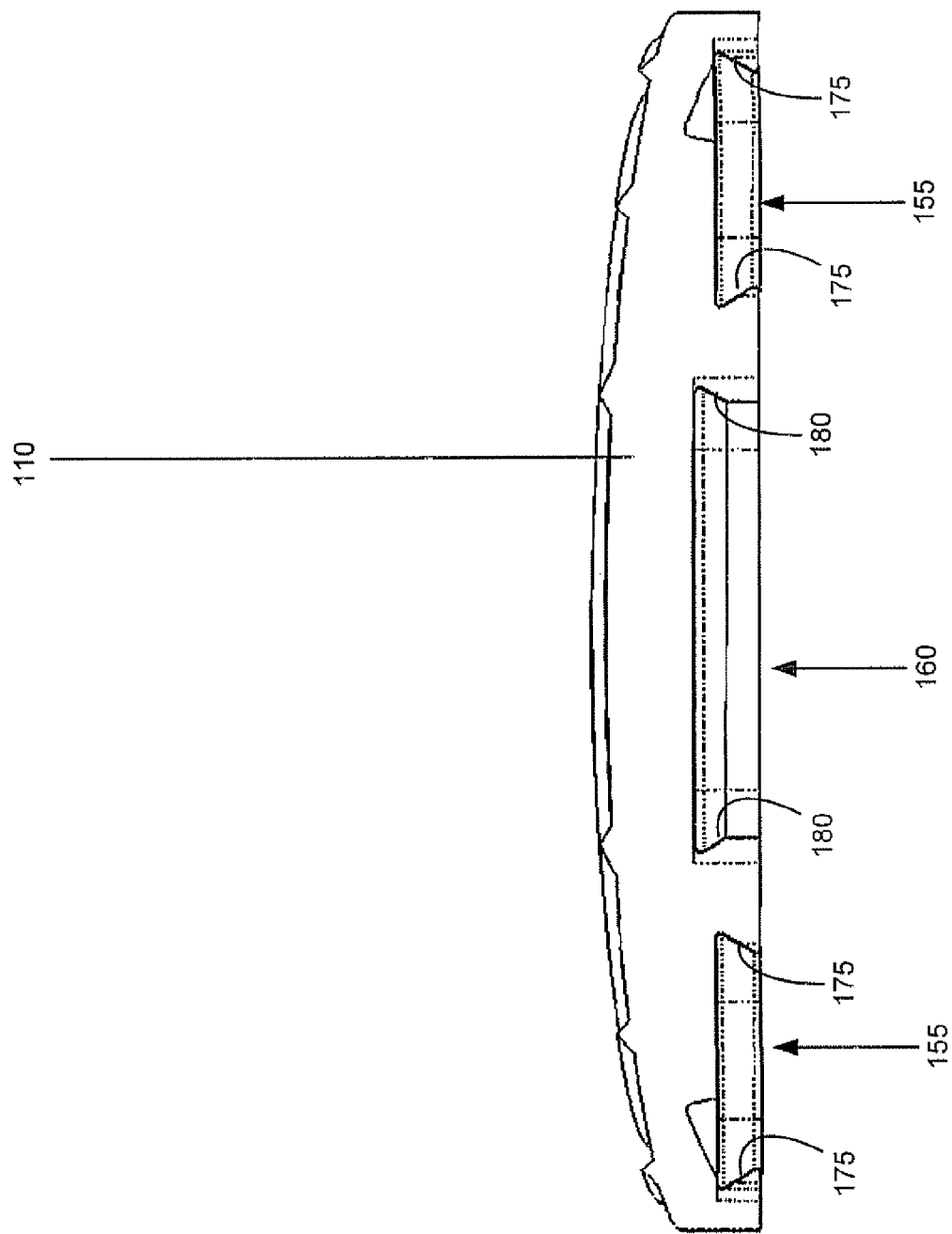
FIG. 4 is a diagrammatic representation of an end view of one embodiment of an implant plate.

FIG. 4 is a diagrammatic representation illustrating an end view of one embodiment of implant plate 110. Assuming implant plate 110 is used in an anterior approach procedure, FIG. 4 is an anterior end view. As shown in FIG. 4, implant plate 110 includes channels 155 open to the anterior end with dovetailed walls 175. Similarly, implant plate 110 includes channel 160 open to the anterior end with dovetailed walls 180. Walls 175 and 180 are angled so that the respective channels are wider closer to the outer face than the inner side of implant plate 110. Channels 155 and 160 can be otherwise shaped to respectively receive the insertion device and spacer member 115.

Figure 5:
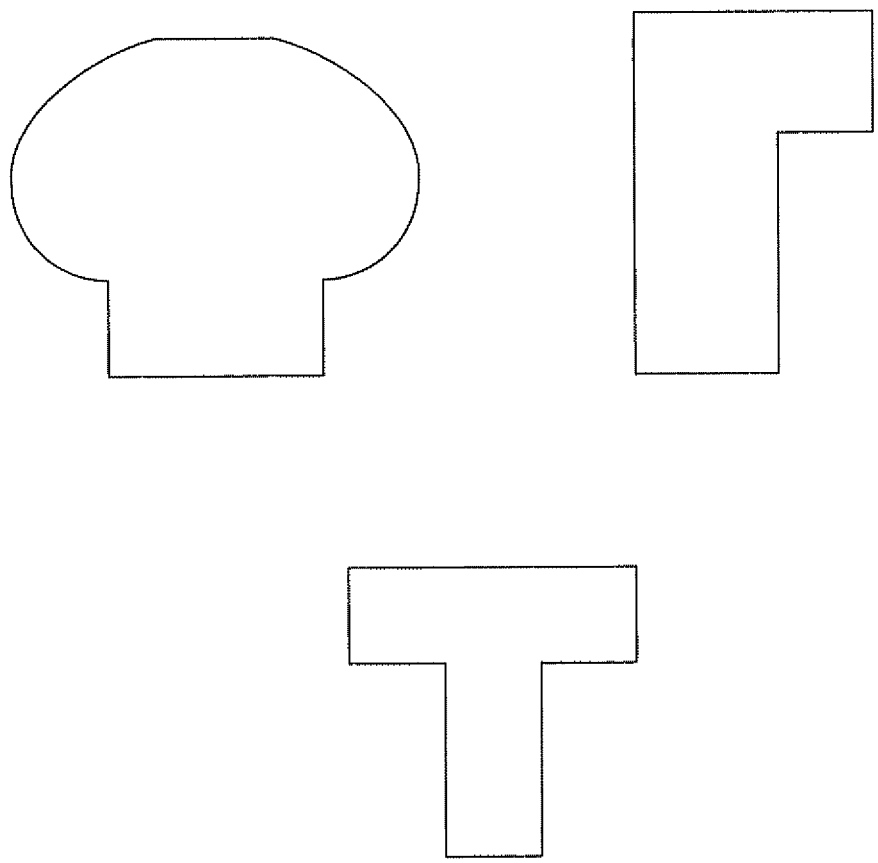
FIG. 5 is a diagrammatic representation of various embodiments of channel shapes.

FIG. 5 is a diagrammatic representation of end views of other example channel shapes for receiving the insertion device or spacer member 115. Keyhole, "T", and partial "T" shapes are shown. The embodiments of FIG. 5 are provided by way of example and not limitation.

Figure 6:
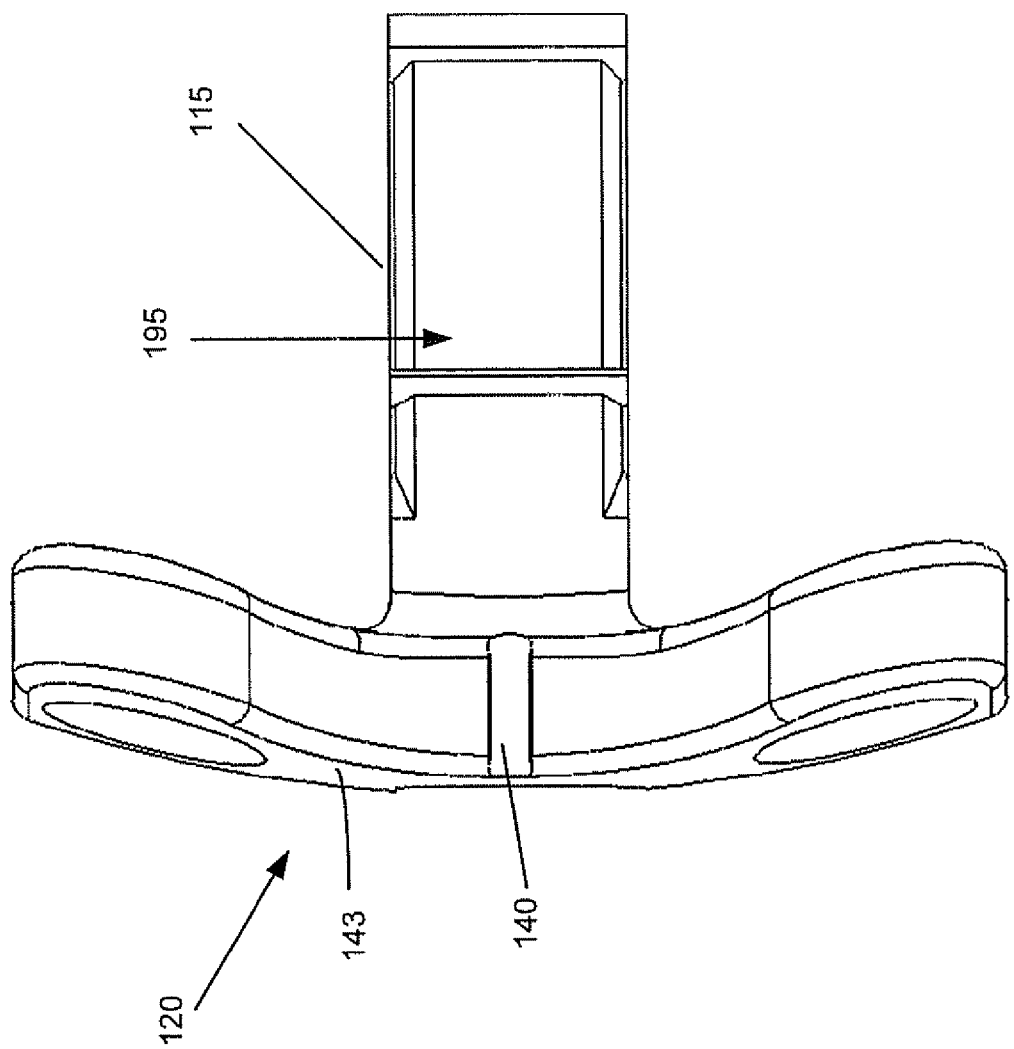
FIG. 6 is a diagrammatic representation of a cross-sectional view of one embodiment of an integrated end plate and spacer member.

FIG. 6 is a diagrammatic representation of a cross-sectional view of one embodiment of an integrated end plate 120 and spacer member 115. End plate 120 can have be flat, curved or other suitable form factor for spinal surgery. Spacer member 115 can be connected to or be integrated with plate 120. The size of spacer member 115 can be selected to provide the appropriate distance between implant plates 110 and 112 and depth of insertion. Additionally, spacer member 115 can be shaped so that a desired lordotic angle is achieved when implant 100 is inserted. For example, spacer member 115 can be a partial wedge shape so that the anterior height of spacer member 115 is different than the posterior height of spacer member 115. Spacer member 115 can include a cavity 195 that can be packed with bone growth material. End plate 120 can include a passage 140 that opens to outer surface 143 of end plate 120 and the center of spacer member 115 to allow access to cavity 195.

Figure 7:
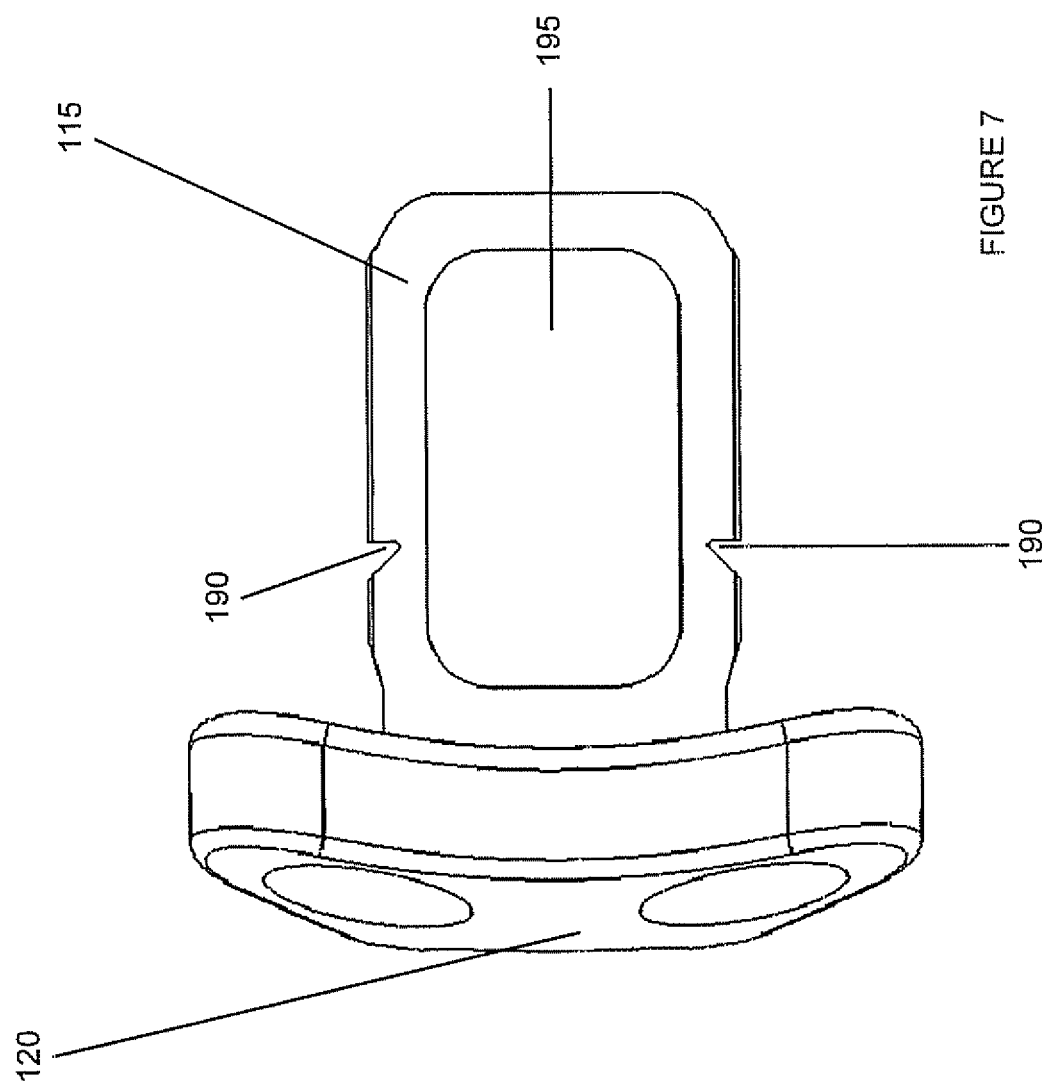
FIG. 7 is a diagrammatic representation of a top view of one embodiment of an integrated end plate and spacer member.

FIG. 7 is a diagrammatic representation of a top view of integrated end plate 120 and spacer member 115. Spacer member 115 can include indents 190 to capture protrusion 170 of implant plate 110 (shown in FIG. 3). As illustrated in FIG. 7, spacer member 115 can also form a cavity 195. Bone growth or other material can be packed in cavity 195.

Figure 8:
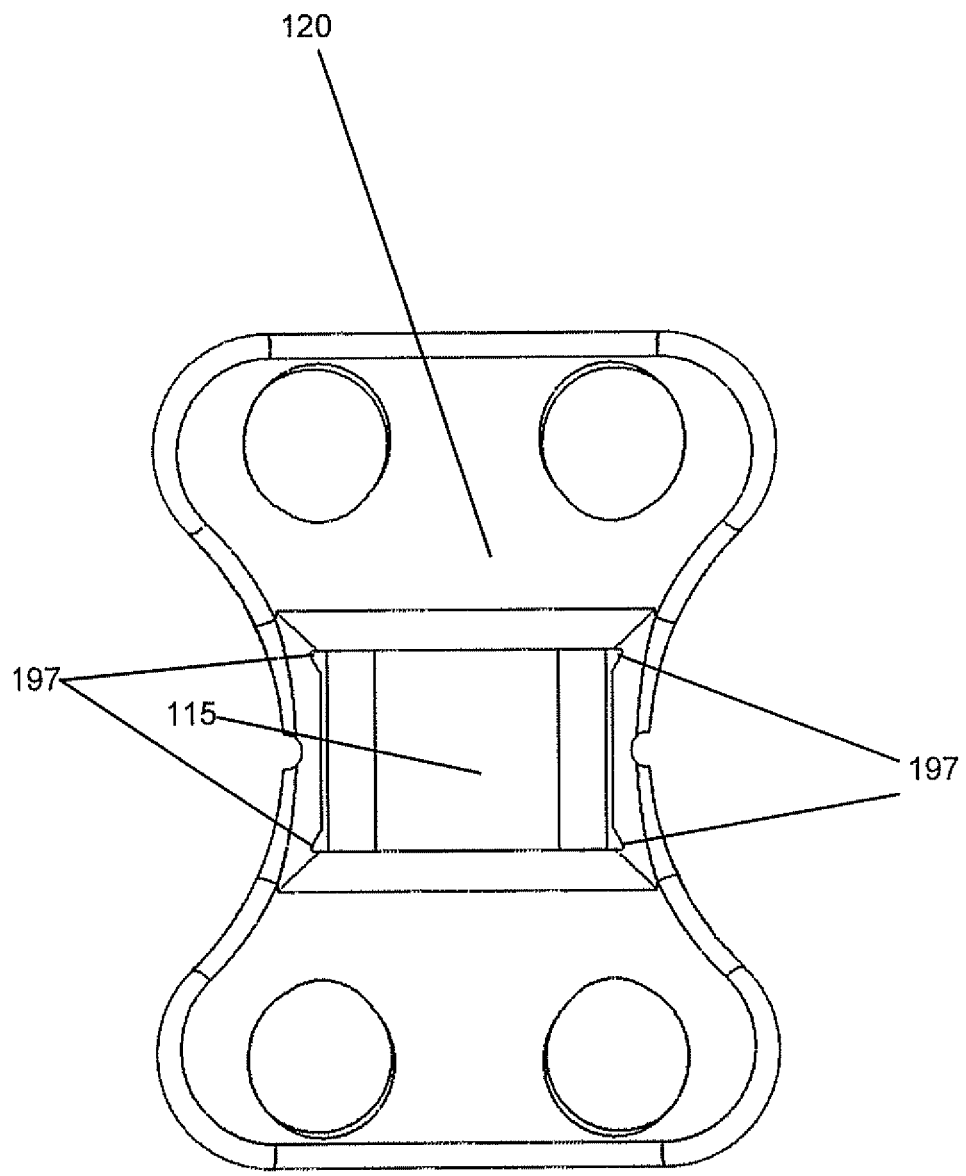
FIG. 8 is a diagrammatic representation of and end view of one embodiment of an integrated end plate and spacer member.

FIG. 8 is a diagrammatic representation of an end view of integrated end plate 120 and spacer member 115. For an anterior procedure, FIG. 8 represents a posterior view. Spacer member 115, according to one embodiment, has a complementary shape to channel 160 of the implant plates 110 and 112 so that a portion of spacer member 115 is captured by the sidewalls of channel 160. For example, spacer member 115 can include tapered (or other shaped) flanges 197 that are captured by the dovetailed sidewalls of the respective channels 160. When in place, the joint formed by channels 160 and flanges 197 prevent the implant plates from vertically separating from spacer member 115.

End plate 120 can have a "bow" shape in which the upper and lower portions of end plate 120 are wider than the center portion. As discussed below in conjunction with FIG. 11, this allows end plate 120 to limit the separation distance of an insertion tool.

Figure 9:
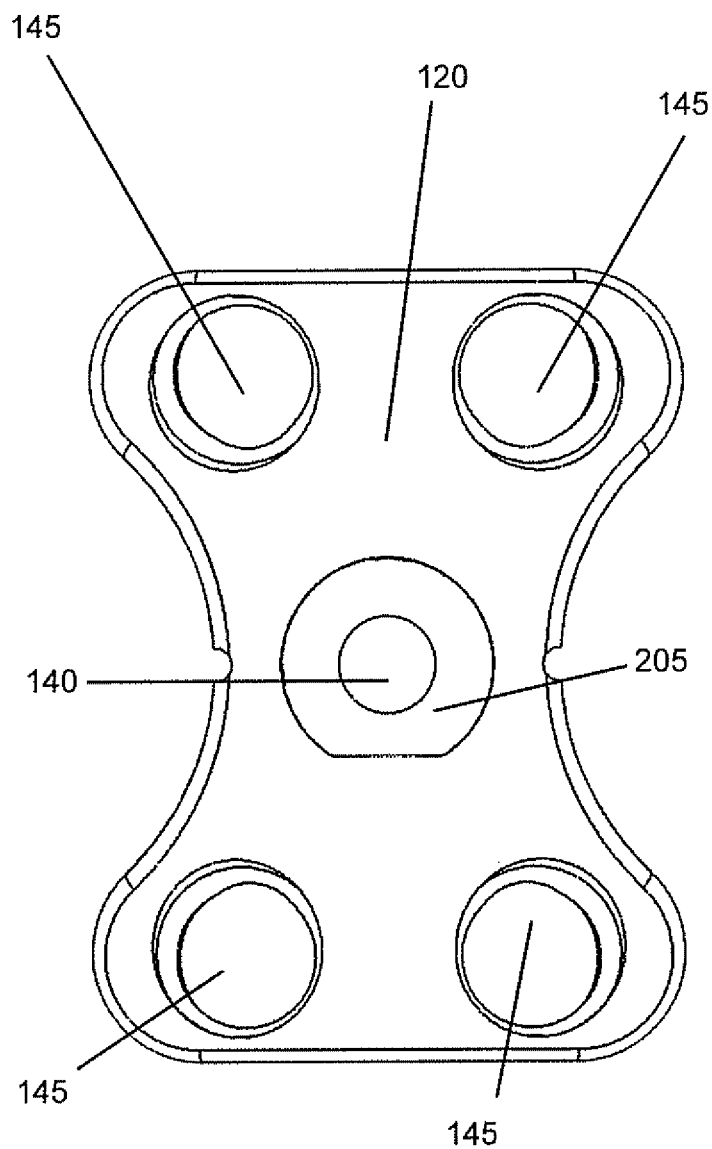
FIG. 9 is a diagrammatic representation of another end view of one embodiment of an integrated end plate and spacer member.

FIG. 9 is a diagrammatic representation of an end view of end plate 120. For an anterior procedure, FIG. 9 represents an anterior view. End plate 120 can include fastener holes 145 to allow end plate 120 to be fastened to adjacent vertebrae. Additionally, end plate 120 can include an opening to passage 140 to allow access to cavity 195 (shown in FIG. 7). End plate 120 can also include recessed feature 205 that can aid in alignment of a driver during insertion of spinal implant 100.

Figure 10:
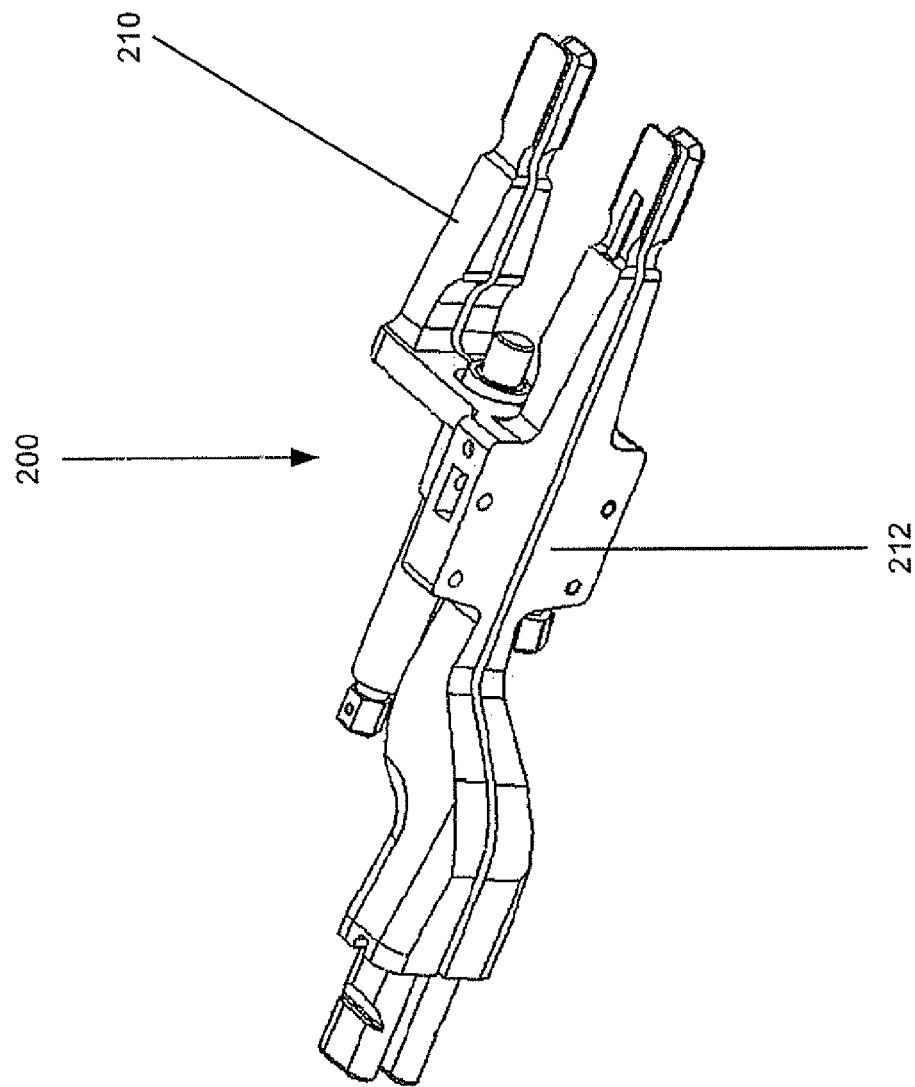
FIG. 10 is a diagrammatic representation of one embodiment of an insertion tool.

FIG. 10 is a diagrammatic representation of one embodiment of a separator 200 (i.e., a portion of an insertion device) to insert implant 100. Separator 200 can include arms 210 and 212. Arms 210 and 212 can include respective attachment portions that couple separator 200 to respective arms of a spreader using a friction fit, mating fit or other suitable connection mechanism. Arm 210 couples to implant plate 110 and arm 212 couples to implant plate 112 (e.g., through frictional connections or other connections). End plate 120 and spacer member 115 are movably captured in a channel formed in separator 200 so that end plate 120 and spacer member 115 can slide toward implant plates 110 and 112.

Figure 11:
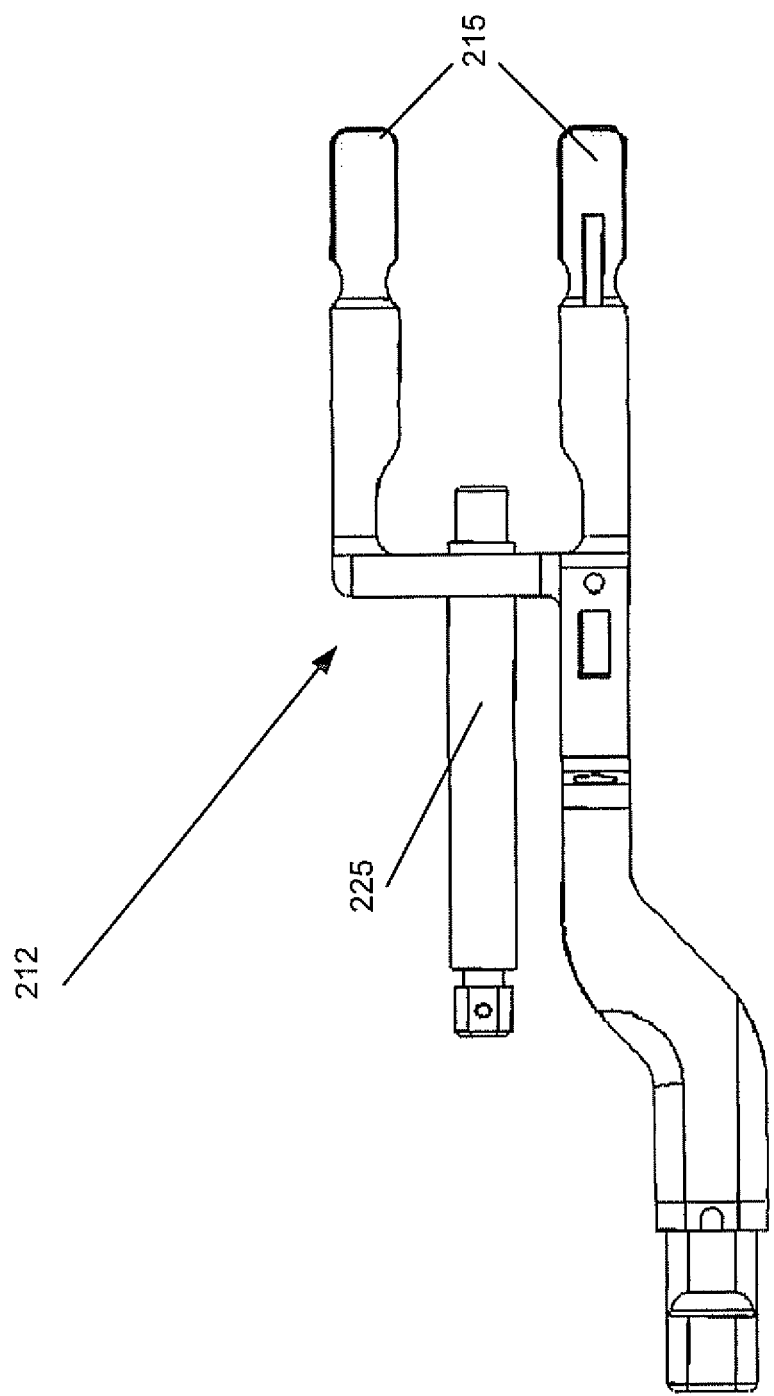
FIG. 11 is a diagrammatic representation of one embodiment of an arm of an insertion tool.

FIG. 11 is a diagrammatic representation of a bottom view of one embodiment of arm 212. Arm 212 can include prongs 215 shaped to fit corresponding channels in implant plate 112 (e.g., channels 155 shown in FIG. 3). According to one embodiment, prongs 215 can be separated by a distance that is sufficient to straddle the center portion of end plate 120 but not the top and bottom portions of end plate 120. Put another way, the gap between prongs 215 is greater than the width of the center of end plate 120 but less than the width of the top and bottom portions of end plate 120. Consequently, prongs 215 (and the corresponding prongs on the arm 210) form a channel down which end plate 120 and the integrated or connected spacer member 115 can move. The bow shape or other shape of end plate 120 limits the separation distance of arms 210 and 212.

Arm 212 can define a passage 225. This passage can allow a driver (e.g., a slap hammer or other driver) access to end plate 120. The driver can assert a force on end plate 120 to move end plate 120 into position during implantation. Additionally, passage 225 allows materials to be added to end plate assembly 120. For example material can be injected through passage 225, passage 140 (shown in FIG. 2) into cavity 195 formed by spacer member 115 (shown in FIG. 7).

Figure 12A:
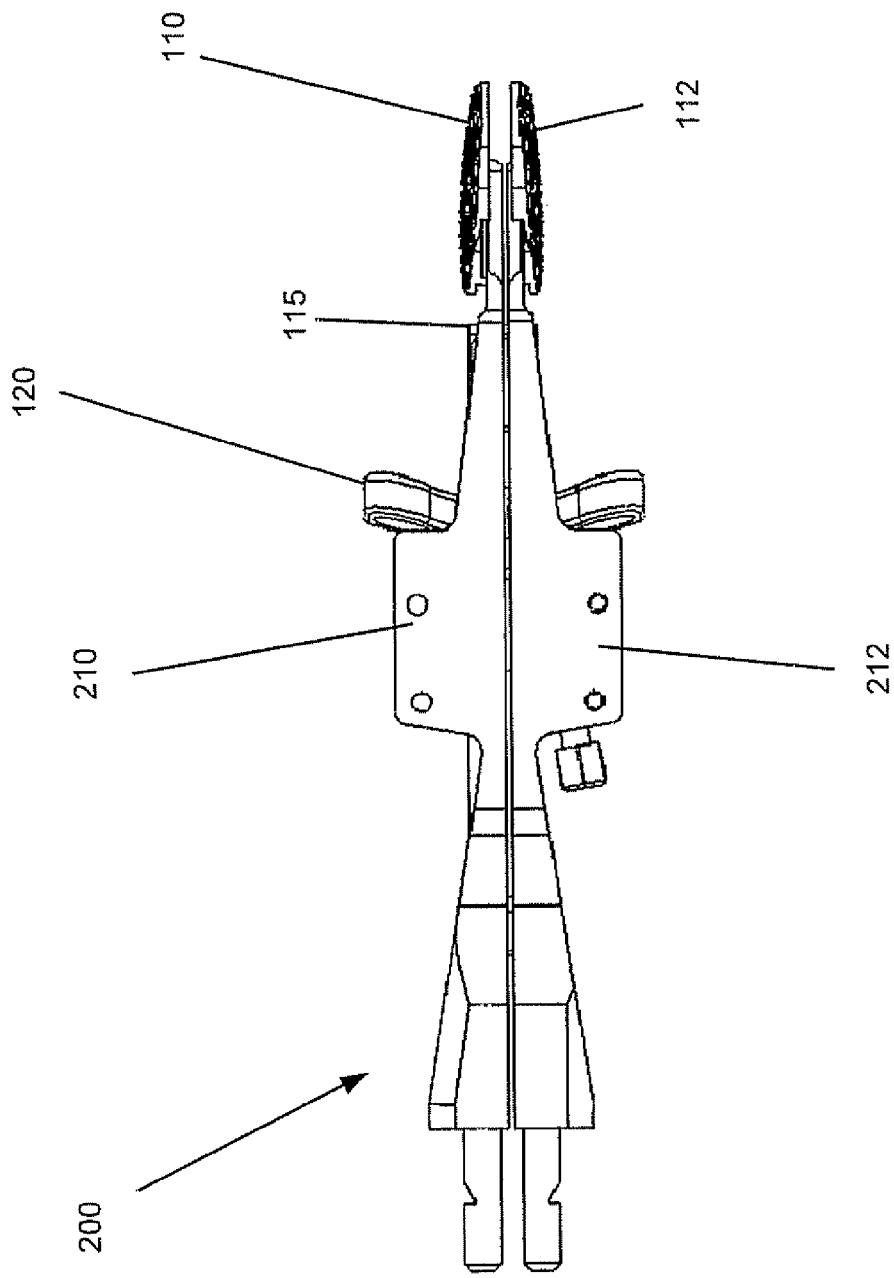
FIGS. 12a-12c are diagrammatic representations of an insertion tool and spinal implant in various stages of an insertion process.
Figure 12B:
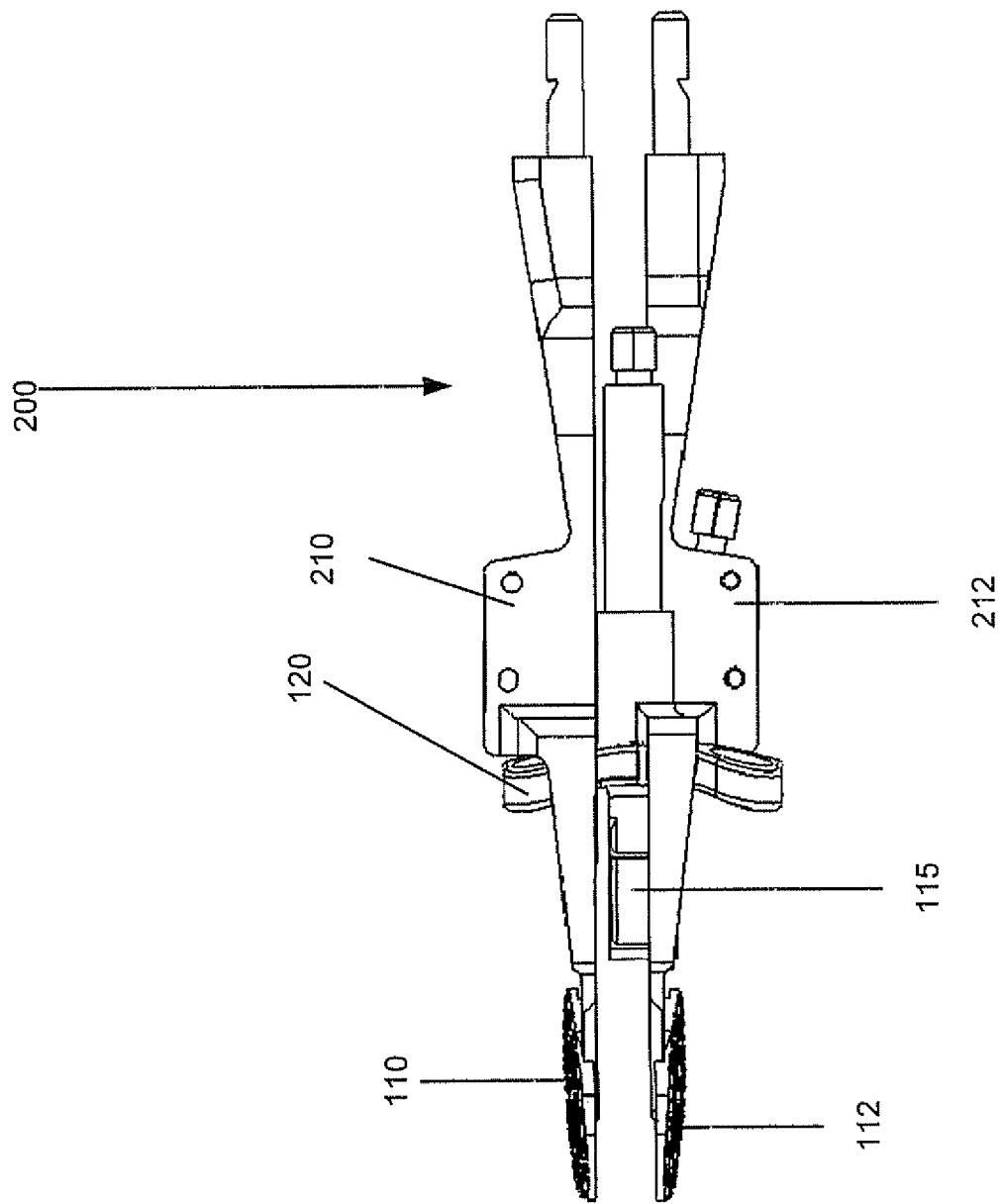
Figure 12C:
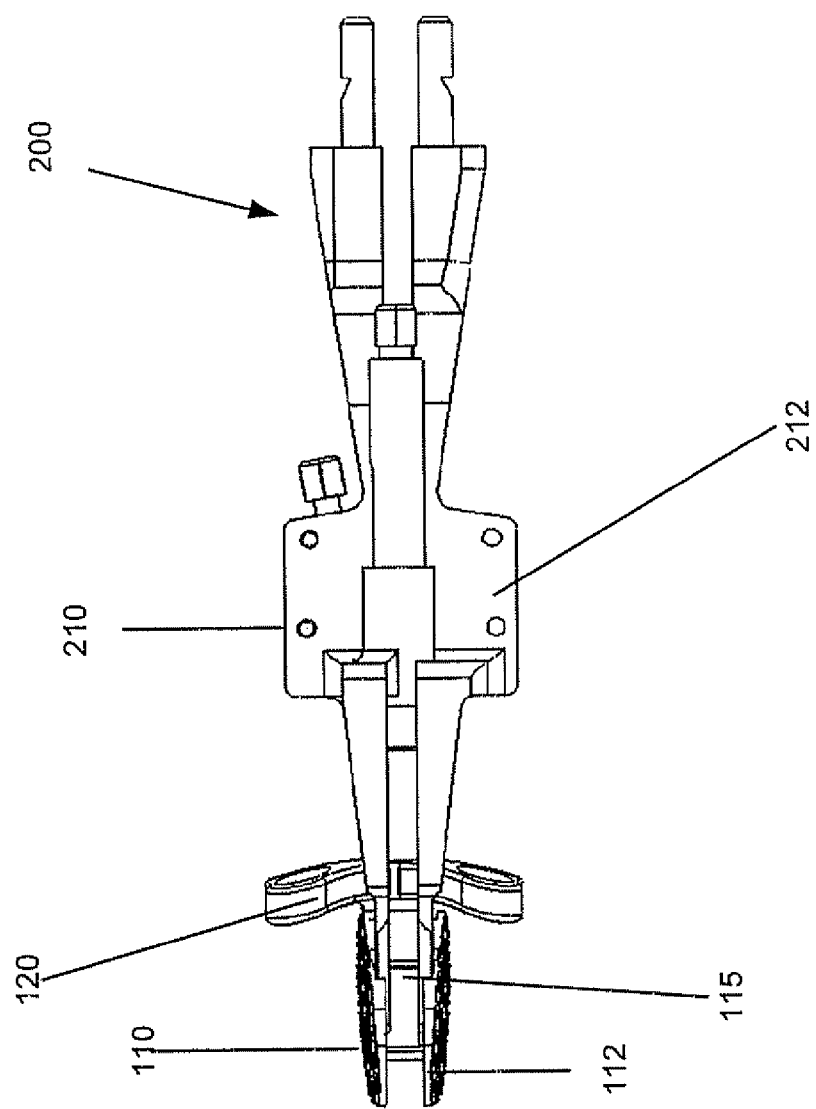

FIGS. 12a-c illustrate one embodiment of separator 200 and implant 100 during various stages of insertion. FIG. 12a illustrates separator 200 from one side and FIGS. 12b and 12c illustrate separator 200 from the opposite side during the procedure. In operation, a surgeon can make an incision on the anterior side of the body during a discectomy procedure. Implant plates 110 and 112, end plate 120 and spacer member 115 can be loaded on separator 200 (FIG. 12a) and separator 200 inserted into the body using a spreader such that implant plates 110 and 112 are inserted in the space created by removal or partial removal of a vertebral disc. Arms 210 and 212 are separated to separate implant plates 110 and 112 (FIG. 12b). The separation distance can be limited by the geometry of end plate 120 or through another suitable mechanism. When implant plates 110 and 112 are separated, spacer member 115 can be moved to join with implant plates 110 and 112 (FIG. 12c). End plate 120 can then be attached to the vertebral bodies using fasteners. Separator 200 can be removed from implant plates 110 and 112. Various portions or all of separator 200 and implant 100 may be radiopaque or include radiopaque markers to allow viewing with medical imaging devices to ensure proper placement of implant 100.

Figure 13:
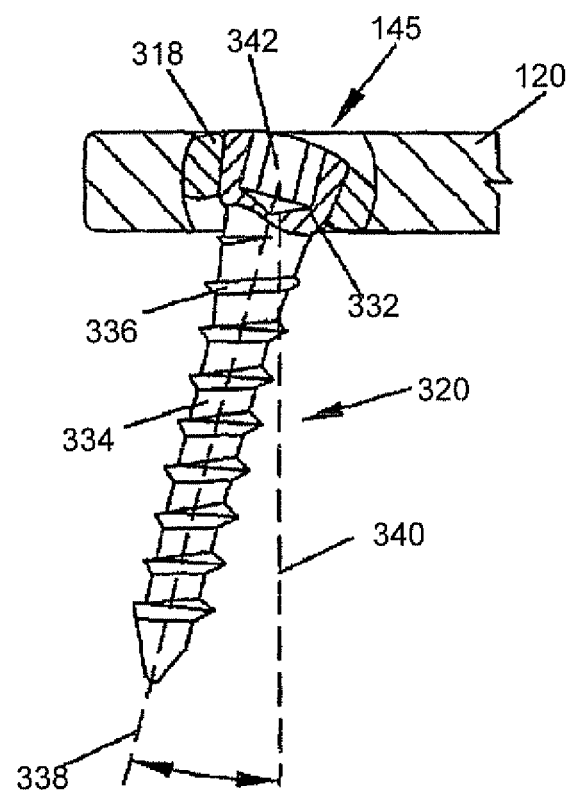
FIG. 13 is a diagrammatic representation of one embodiment of a bone screw attached to an end plate.
Figure 14:
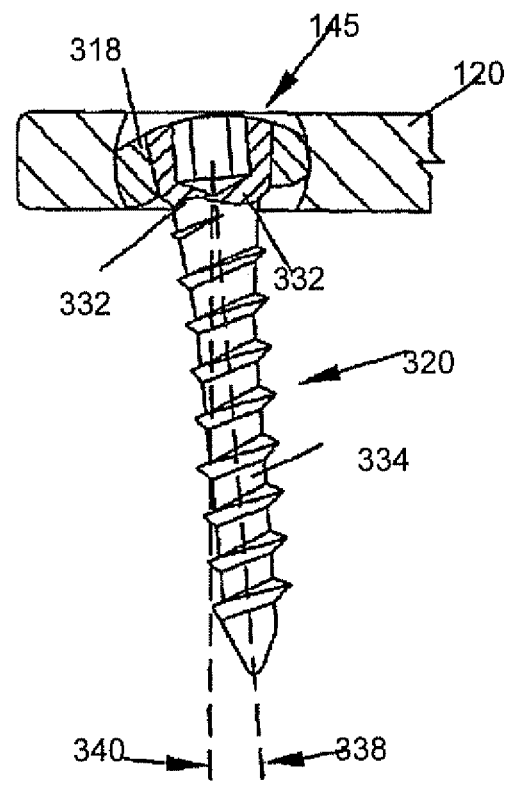
FIG. 14 is a diagrammatic representation of another embodiment of a bone screw attached to an end plate.

As discussed above, end plate 120 can be attached to the bones using fasteners that rotate to allow better alignment of end plate 120. FIG. 13 depicts a cross-sectional view of an embodiment of one of the holes 145 (also shown in FIG. 2) in which screw 320 is disposed. Hole 145 is preferably substantially spherical in shape so that a head 332 of screw 320 may be rotated and moved to various positions within borehole 312. Ring 318 is preferably sized to fit into hole 145 between plate 120 and head 332. The outer surface of ring 318 is preferably curved to permit movement of the ring within hole 145. The combination of ring 318 and hole 145 is like that of a ball and socket since ring 318 may be rotated both horizontally and vertically in clockwise and counterclockwise directions within hole 145. Ring 318 may also be rotated in directions that are angled away from the horizontal and vertical directions. In FIG. 13, ring 318 at least partially surrounds head 332 of screw 320 which is positioned within hole 145. A shank 334 of bone screw 320 preferably has threading 336 to allow the screw to be inserted into a bone when it is rotated in a clockwise direction. Head 332 preferably includes a cavity 342 that extends from the top of the head to an inner portion of the head. Cavity 342 may be shaped to receive the end of any fastening device e.g., a socket wrench that may be used to turn screw 320. Screw 320 may be simultaneously screwed into a bone and moved to its desired position. The inner surface of ring 318 and the outer surface of head 332 are preferably tapered and shaped to mate with each other. The bottom portion of head 332 is preferably smaller than the upper portion of ring 318. As screw 320 is inserted into a bone, head 332 preferably applies a radial force to ring 318, thereby causing the ring to expand within the hole and increase the size of the gap in ring 318 that allows ring 318 to expand. An interference fit may form between screw head 332, ring 318, and plate 120 in which these elements fit so tightly together that they obstruct the movements of each other. The hoop stress of ring 318 on head 332 may fixedly attach screw 320 to plate 120. Also during insertion of screw 320, screw head 332 and ring 318 may be positioned within hole 145 such that their left sides are at a higher elevation than their right sides. FIG. 13 shows that positioning screw head 332 in this configuration may result in a centerline 338 of shank 334 being obliquely angulated with respect to plate 120. In fact, centerline 338 may be positioned where it is at an angle ranging from 0 to 15 degrees with respect to an imaginary axis 340 which is perpendicular to plate 120. FIG. 13 demonstrates shank 334 of screw 320 being angled to the left of imaginary axis 340 while FIG. 14 demonstrates shank 334 being angled to the right of imaginary axis 340. Screw 320 is not limited to these positions and can be angled in various directions, such as into the page.

Figure 15:
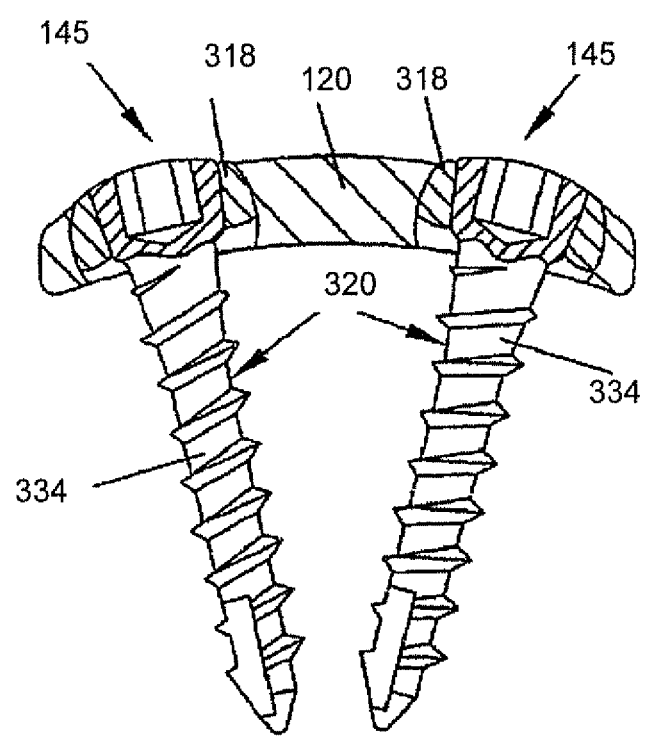
FIG. 15 is a diagrammatic representation of an embodiment of multiple bone screws attached to an end plate.
Figure 16:
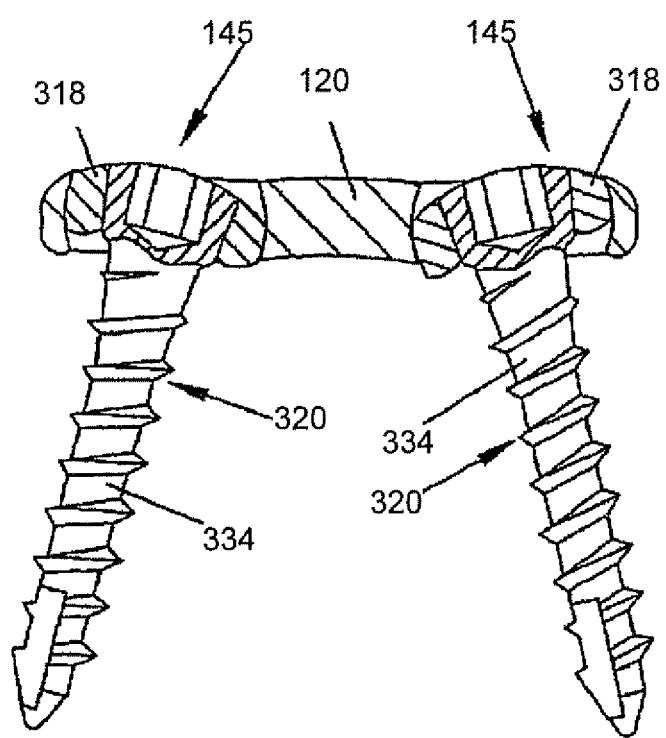
FIG. 16 is a diagrammatic representation of another embodiment of multiple bone screws attached to an end plate.

FIGS. 15 and 16 depict different embodiments of end plate 120 with fasteners inserted. FIG. 15 shows that screws 320 may be positioned within holes 145 such that they extend in converging directions with respect to each other. The screws 320 depicted in FIG. 16, on the other hand, are shown as being positioned such that their shanks 334 extend in diverging directions with respect to each other. Screws 320 may be moved to such positions as described above. Since bone screws 320 may be placed in diverging or converging directions through holes 145 at both ends of plate 120, screw backout may be greatly reduced. Further, the use of rings 318 to fixedly attach screws 320 to plate 120 may prevent damage to tissue structures by any screws that are able to escape from the bone. Rings 318 preferably do not extend above the upper surface of plate 120, and thus advantageously do not contact tissue structures. Screw 320 may be placed in a uni-cortical position within the bone since the problem of screw backout is greatly reduced by the diverging or converging screw configurations.

According to one embodiment, end plate 120 is prepared for surgical implantation by pre-positioning of rings 318 within holes 145. During the actual surgical procedure, holes may be drilled and tapped into the bones to which plate 120 is to be attached. Plate 120 may then be positioned adjacent to the bones when spacer member 115 is coupled to implant plate 110 and implant plate 112. Each of the screws 320 may be screwed into the bone holes while they are being positioned within their corresponding holes 145. Each pair of screws 320 at opposite ends 120 may be positioned so that shanks of the screws are at oblique angles relative to the plate. The insertion force of each screw 320 into each ring 318 preferably causes the ring to exert a compressive force on the screw head, thereby fixably connecting the screws to plate 120.

Figure 17:
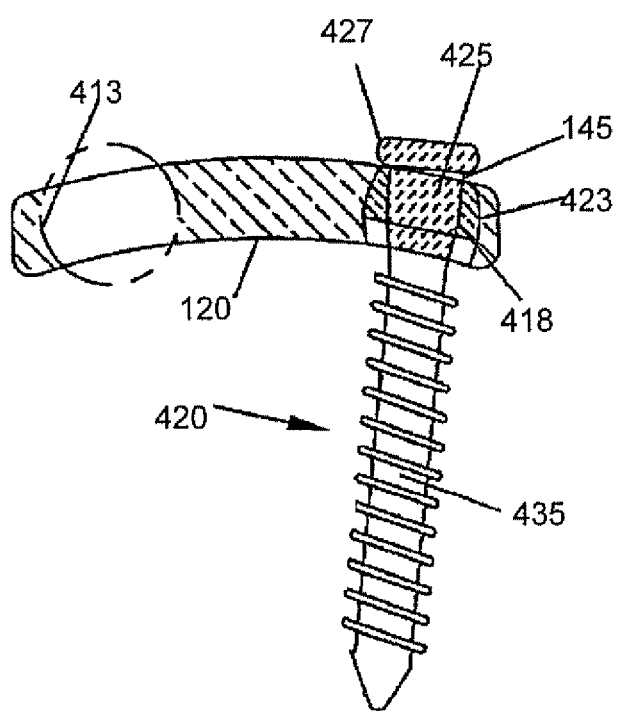
FIG. 17 is a diagrammatic representation of another embodiment of a bone screw and end plate.

A side view of another embodiment of a spinal plate 120 and fasteners is shown in FIG. 17. This embodiment includes a bone screw 420 and a ring 418. Plate 120 may be used to stabilize a bony structure such as the spine to facilitate a bone fusion (e.g., a spinal fusion). The bone screw 420 may be used to connect plate 120 to a bone such as a vertebra. Ring 418 preferably fixes bone screw 420 to plate 120 at a selected angle that depends upon the patient's anatomy.

In this embodiment, each hole 145 preferably has a curvate inner surface 413 for engaging the outer surface 423 of ring 418. The inner surface 413 preferably has the shape of a portion of an outer surface of a sphere. Hole 145 has a width that is defined across the inner surface 413 of the borehole. The width of the borehole may vary in a direction axially through the borehole. For example, the width of the holes preferably increases from a surface of the plate to about the middle of the plate. The width of the hole 145 preferably decreases from about the middle of the plate to an opposite surface of the plate such that the hole has a maximum width near the midpoint between the surfaces.

The outer surface 423 of ring 418 is preferably curvate for engaging the inner surface 413 of the borehole. The shape of surfaces 423 and 413 preferably allow ring 418 to swivel within the borehole. The swiveling action may be similar to that of a ball and socket joint. The ring preferably surrounds at least a portion of the head 425 of a bone screw. The enlarged end 427 disposed on head 425 is optional and need not be included if it inhibits angulation of the bone screw. The swiveling of the ring within the borehole preferably enables the shank 435 of the bone screw 420 to rotate in a substantially conical range of motion. In this manner, the head is preferably movable within the borehole, and the shank is adjustably positionable at a plurality of angles substantially oblique to the plate.

In an embodiment, the surfaces 423 and 413 are preferably shaped to provide a conical range of motion to the shank that is within a preferred range of angles. The head is preferably movable within the borehole such that the shank can be positioned at a selected angle relative to an imaginary axis running perpendicular to the plate proximate borehole 145. The selected angle is preferably less than about 45 degrees, more preferably less than about 30 degrees, and more preferably still less than about 15 degrees.

Ring 418 preferably has an outer width that is less than or about equal to the width of hole 145 at a location between the surfaces of plate 120. In this manner, ring 418 may be positioned within hole 145 proximate the middle of the hole to enable the bone screw 420 to extend substantially perpendicularly from the bone plate 120. Prior to surgery, rings 418 are preferably pre-positioned within holes 145 of plate 120, "Pre-positioned" is taken to mean that the rings are capable of swiveling within the borehole but are preferably inhibited from falling out of the borehole because of the reduced width of the borehole proximate the upper and lower surfaces. The width of the borehole proximate the upper and lower surfaces of plate 120 is preferably less than or about equal to the outer width of the ring to inhibit the ring from falling out of the borehole. In this manner, the surgeon may use a plate 120 having rings 418 pre-positioned within the holes 145 such that the rings will not fall into the surgical wound when implant 100 is installed.

Alternately, the rings 418 can be manually positioned within holes 145 during surgery. Ring 418 preferably includes one or more slots or gaps. The slot preferable allows the ring to be contracted or expanded. Contraction of ring 418 may allow the ring to be positioned within the borehole during surgery. Once positioned within the borehole the ring preferably expands and is inhibited from falling out of the borehole.

The ring 418 is preferably capable of being swiveled such that one portion of the ring is adjacent to one surface of plate 120 while another portion of the ring lies adjacent to the opposite surface of plate 120. Ring 418 is preferably sufficiently thin to allow it to reside within the borehole without extending from the borehole beyond the surfaces of plate 120. Generally, it is preferred that the ring and screw head remain within the hole 145 to minimize the profile of implant 100. In some embodiments, however, the bone screw 420 may be capable of being angulated relative to the plate 120 such that ring 418 extends from the hole 145 beyond a surface of the plate 120.

The head 425 is preferably screwed into ring 418 to create a fixed connection between bone screw 420 and plate 120 at a selected angle. In an embodiment depicted in FIG. 18, screw head 425 preferably contains head threading 421 on its outer surface that is complementary to ring threading 419 contained on the inner surface of ring 418. The head threading 421 preferably mates with the ring threading 419 to enhance the connection between the bone screw 420 and the ring 418. The head 425 preferably has a cavity 442 formed on its upper surface for receiving a driving tool such as a screw driver or an alien wrench.

Figure 18:
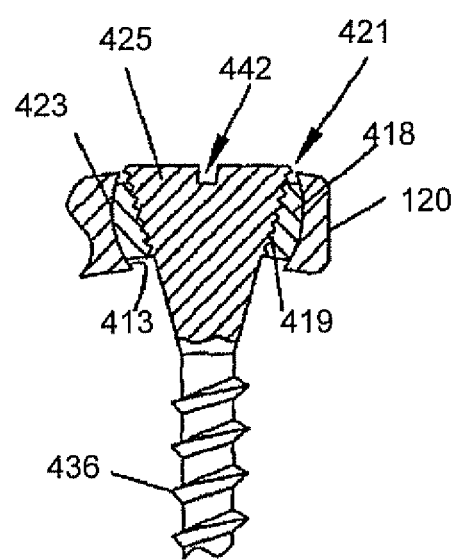
FIG. 18 is a diagrammatic representation of yet another embodiment of a bone screw and end plate.

It is believed that using a threading engagement between the head 425 and ring 418 increases the hoop stress exerted on head 425, resulting in a stronger connection between the bone screw 420 and the plate 120. Moreover, if bone threading 436 becomes loose within a bone, screw backout from plate 120 will tend to be resisted by the threaded connection between the screw head 425 and the ring 418. Thus, even if the shank 435 loosens within the bone, the head will tend to remain within the borehole of the plate so as not to protrude from the plate into surrounding body tissue. As shown in FIG. 18, the head threading 421 on the head 425 and the ring threading 419 on the inner surface of ring 418 is preferably substantially fine relative to the threading 436 on bone screw 420. That is, the pitch of the head threading 421 and ring threading 419 is preferably smaller than that on bone screw 420. The ring threading 419 preferably has multiple starts to facilitate connection of the bone screw and the ring. In one embodiment, the ring threading 419 has a double start such that the head can be started into the ring threading at either one of two orientations offset by 180 degrees. In another embodiment, the ring threading has a triple start such that the head can be started into the ring threading at any one of three orientations offset by 420 degrees.

The ring threading 419 and head threading 421 are preferably pitched to a substantially similar degree to the threading 436 on the bone screw 420. Preferably, the ring threading 419 and head threading 421 are pitched such that the head 425 causes expansion of the ring 418 while the bone screw 420 is being inserted into the bone.

During the surgical procedure for attaching the plate 120 to a bone, holes may be drilled and tapped into the bones to which plate 120 is to be attached. Plate 120 may then be positioned adjacent to the bones. A ring 418 may be positioned within the borehole. A bone screw 420 may be positioned through ring 418 such that the head threading 421 of head 425 engages the ring threading 419 of ring 418. The bone screw 420 may then be rotated to insert the bone screw into the bone. As the screw is rotated the head threads and ring threads preferably interact such that the head is moved into the ring. Movement of the head 425 into the ring 418 preferably causes the ring to expand such that the orientation of the bone screw 420 relative to the plate 120 is fixed. Preferably, the ring threading and head threading is pitched such the orientation of the bone screw 420 is fixed after plate 120 engages the bone.

The bone screws may be used in pairs to prevent screw backout. The bone screws are preferably positioned into the bone in substantially converging or substantially diverging directions relative to one another.

The outer surface of the head 425 is preferably tapered so that screwing the head into the ring causes a change in width (e.g., expansion) of the ring 418 to fix the bone screw 420 in position relative to the plate 120. The inner surface of the ring 418 may also be tapered to substantially match the taper on the outer surface of the head. At least a portion of the head 425 preferably has a width greater than the inner width of the ring 418. As the screw head is screwed into the ring 418, the ring preferably expands outwardly from its inner surface to accommodate the increasing width of the screw head 425. The ring 418 may contain a slot or gap as previously described to facilitate expansion of the ring against the inner surface 413 of the hole 145. The slot is preferably widened as a result of force received from head 425. The force exerted by head 425 against the inner surface of ring 418 preferably presses the ring into a fixed engagement against inner surface 413 of hole 145.

Figure 19:
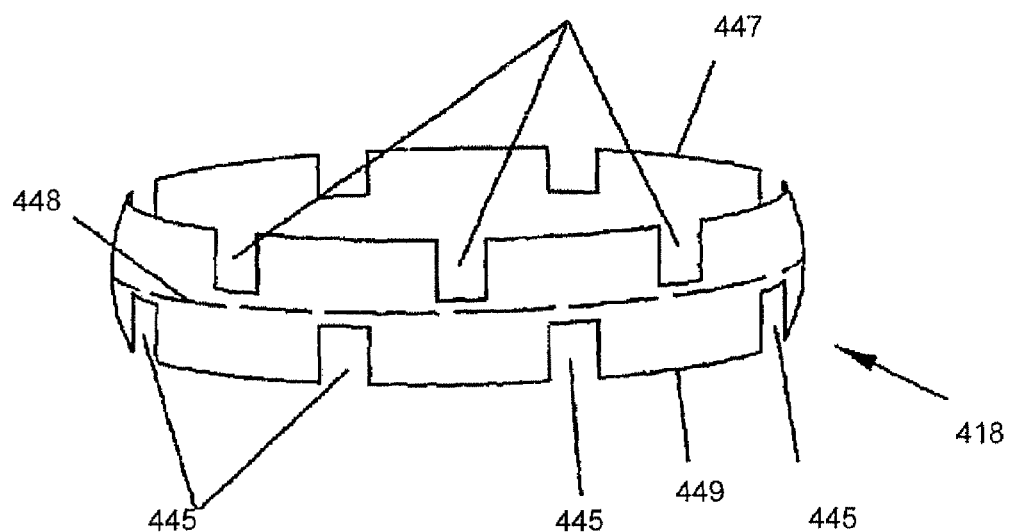
FIG. 19 is a diagrammatic representation of an embodiment of a ring.

Alternatively, ring 418 may contain one or more partial slots 445, as depicted in FIG. 19. Each partial slot 445 preferably extends from a top 447 or bottom 449 of ring 418 into the ring. Partial slots may extend up to about midpoint 448 of ring 418. In one embodiment, a plurality of slots 445 may be oriented about the ring such that alternate slots extend from the top 447 and/or the bottom 449 of ring 418, as depicted in FIG. 19. These alternating partial slots preferably facilitate the expansion and contraction of ring 418.

Figure 20A:
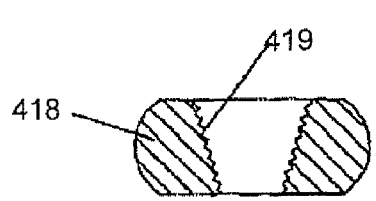
FIGS. 20a-20b are diagrammatic representations of cross-sectional views of various embodiments rings.
Figure 20B:
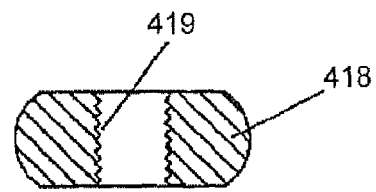
Figure 21A:
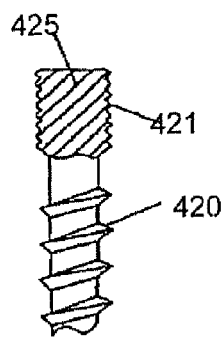
FIG. 21a-21b are diagrammatic representations of cross-sectional views of various embodiments of bone screw heads.
Figure 21B:
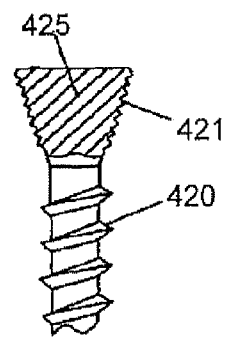

Cross-sectional views of two embodiments of ring 418 having threaded section 419 are shown in FIGS. 20A and 20B. The ring may contain an inner surface that is tapered (as shown in FIG. 20A) or that is substantially untapered (as shown in FIG. 20B). Cross-sectional views of two embodiments of screw 420 are shown in FIGS. 21A and 21B. The head 425 may have a substantially untapered outer surface (as shown in FIG. 21A) or a substantially tapered outer surface (as shown in FIG. 21B). It is to be understood that each of the heads of the screws depicted in FIGS. 21A and 21B may be used in combination with either of the rings 418 depicted in FIGS. 20A and 20B. It is also to be appreciated that the head of the screw may include an outer surface having a substantially untapered portion along with a tapered portion proximate its end for expanding the ring 418.

As described herein, a "ring" is taken to mean any member capable of fitting between the inner surface 413 of a fastener hole and the bone screw 420 to connect the bone screw to the plate 120. The ring is preferably substantially circular to surround head 425, but the ring may instead have a non-circular shape. The ring may be made of a number of biocompatible materials including metals, plastics, and composites.

Figure 22:
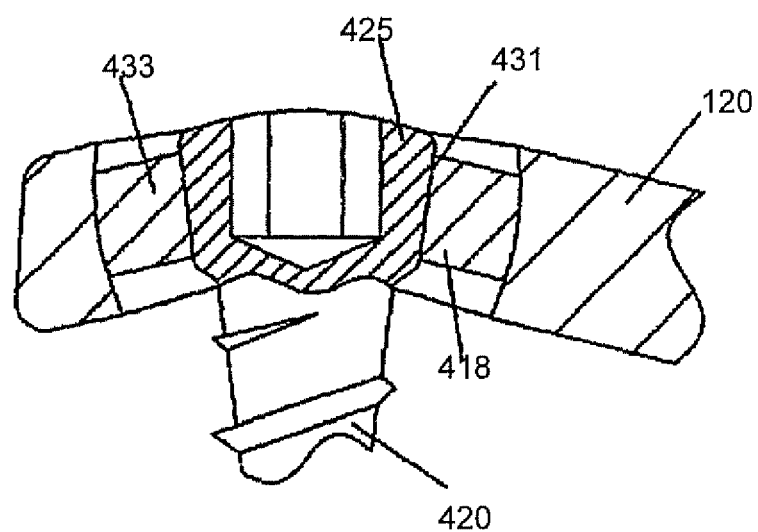
FIG. 22 is a diagrammatic representation of another embodiment of a bone screw and end plate.

In an embodiment, a stronger connection between the bone screw 420 and the plate 120 may be formed by texturing either outer surface 431 of head 425 of bone screw 420 or inner surface 433 of ring 418, as depicted in FIG. 22. Preferably, both surfaces are textured to inhibit movement of the bone screw with respect to the plate. During typical manufacturing procedures, outer surface 431 of head 425 and inner surface 433 of ring 418 may be formed as relatively smooth surfaces. While the friction between these smooth surfaces tends to be sufficient to maintain bone screw 420 in a fixed position with respect to plate 120, under stressful conditions the bone screw may be forced out of ring 418. By providing at least one textured surface, the coefficient of friction of the surface may be increased so that a large amount of force is needed to overcome the frictional connection between head 425 of bone screw 420 and ring 418. This increase in friction between bone screw 420 and ring 418 may further inhibit screw backout from plate 120.

A number of textured surfaces may be used to increase the coefficient of friction between ring 418 and head 425 of bone screw 420. In general, any process which transforms a relatively smooth surface into a roughened surface having an increased coefficient of friction may be used. Methods for forming a roughened surface include, but are not limited to: sanding, forming grooves within a surface, ball peening processes, electric discharge processes, and embedding of hard particles within a surface.

In one embodiment a plurality of grooves may be formed in outer surface 431 of head 425 of bone screw 420 or inner surface 433 of ring 418. Preferably, a plurality of grooves is formed in both outer surface 431 and inner surface 433. While it is preferred that both outer surface 431 and the inner surface 433 (is the lead line for 433 in the right place?) be textured, texturing of only one of the surfaces may be sufficient to attain additional resistance to movement.

In another embodiment, the frictional surface may be created by an electrical discharge process. An electrical discharge process is based on the principle of removal of portions of a metal surface by spark discharges. Typically a spark is generated between the surface to be treated and an electrode by creating potential differential between the tool and the electrode. The spark produced tends to remove a portion of the surface disposed between the electrode and the surface. Typically, the electrode is relatively small such that only small portions of the surface are removed. By moving the electrode about the surface numerous cavities may be formed within the surface. Typically these cavities are somewhat pyramidal in shape. Various patterns may be formed within the surface depending on how the electrode is positioned during the discharge. Electric discharge machines are well known in the art. A method for forming a frictional surface within a metal surface using an electric discharge process is described in U.S. Pat. No. 4,964,641 to Miesch et al. which is incorporated by reference as if set forth herein.

A variety of patterns may be formed using an electric discharge machine. Preferably a diamond pattern or a waffle pattern is formed on either inner surface 433 of ring 418 or outer surface 431 of head 425 of bone screw 420.

In another embodiment, inner surface 431 of ring 418 and/or outer surface 433 of head 125 of bone screw 120 may be textured by the use of a shot peening process. A shot peening process for forming a textured surface is described in U.S. Pat. No. 5,526,664 to Vetter which is incorporated by reference as if set forth herein. In general, a shot peening process involves propelling a stream of hardened balls, typically made of steel, at a relatively high velocity at a surface. To create a pattern upon an area of the surface the stream is typically moved about the surface. The speed by which the stream is moved about the surface tends to determine the type of textured surface formed.

Preferably, the stream is moved such that a pattern resulting in a textured surface having ridges and valleys is formed on inner surface 433 of ring 418 and outer surface 431 of head 425 of bone screw 420. When the textured inner surface 431 of ring 418 and the textured head 425 of bone screw 420 are coupled together the ridges and valleys may interact with each other to provide additional resistance to movement in either a longitudinal direction or a direction perpendicular to the longitudinal axis.

In another embodiment, the textured surface may be produced by embedding sharp hardened particles in the surface. A method for embedding sharp hardened particles in a metal surface is described in U.S. Pat. No. 4,768,787 to Shira which is incorporated by reference as if set forth herein. The method of Shira involves using a laser or other high energy source to heat the surface such that the surface melts in selected areas. Just before the molten area re-solidifies, a stream of abrasive particles is directed to the area. In this manner some of the particles tend to become embedded within the molten surface. The particles typically have a number of sharp edges that protrude from the surface after the particles have been embedded within the surface.

Any of the above methods of texturing may be used in combination with another method. For example, outer surface 431 of head 425 of bone screw 420 may be textured using a pattern of grooves. Inner surface of ring 418, however, may be textured using an electrical discharge method. When coupled together the textured surfaces of bone screw 420 and ring 418 may interact with each other to provide additional resistance to movement in either a longitudinal direction or a direction perpendicular to the longitudinal axis.

Textured surfaces may also be formed on any of the other surfaces of the plate system. The formation of textured surfaces preferably increases the frictional resistance between the various components of the plate system.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

What is claimed is:

1. A method of forming a spinal implant comprising:
    inserting a first implant plate having a first spacer channel and a second implant plate having a second spacer channel in a space between adjacent vertebrae;
    distracting the first implant plate and second implant plate from an initial position to a second position with an insertion tool, wherein the insertion tool comprises a first arm and a second arm, wherein the first arm of the insertion tool couples to the first implant plate, and wherein the second arm of the insertion tool couples to the second implant plate;

moving an end plate and spacer member coupled to the end plate along a portion of the insertion tool;

inserting the spacer member in the first spacer channel of the first implant plate and the second spacer channel of the second implant plate;

bringing the end plate in contact with the adjacent vertebrae, wherein the end plate is guided to the adjacent vertebrae by prongs of the first arm of the insertion tool coupled to the first implant plate and prongs of the second arm of the insertion tool coupled to the second implant plate; and fastening the end plate to the adjacent vertebrae.

2. The method of claim 1, further comprising:

inserting the prongs of the first arm into corresponding insertion tool channels of the first implant plate and the prongs of the second arm into corresponding insertion tool channels of the second implant plate, wherein the insertion tool channels of the first implant plate are on either side of the first spacer channel and the insertion tool channels of the second implant plate are on either side of the second spacer channel; and positioning the end plate on the insertion tool so that the prongs inserted in the first implant plate straddle the end plate and the prongs inserted in the second implant plate straddle the end plate.

3. The method of claim 1, wherein distracting the first implant plate and second implant plate comprises separating the first arm and second arm of the insertion tool until separation of the first arm and second arm is limited by the end plate.

4. The method of claim 1, further comprising inserting the spacer member in the spacer member channels at least until complementary features of the first and second implant plates and the spacer member mate to inhibit removal of the spacer member.

5. The method of claim 1, further comprising selecting at least one of the first implant member, the second implant member or the spacer member based on a desired lordotic angle.

6. The method of claim 1, further comprising selecting the spacer member based on a desired spacing between the first implant member and the second implant member.

7. The method of claim 1, wherein the first spacer channel is located at approximately the center of the first implant plate and the second spacer channel is located at approximately the center of the second implant plate.

8. The method of claim 1, wherein the first spacer channel comprises sidewalls shaped to capture at least a first portion of the spacer member and the second spacer channel comprises sidewalls to capture at least a second portion of the spacer member.

9. The method of claim 1, wherein the first spacer channel comprises dovetailed sidewalls and the second spacer channel comprises dovetailed sidewalls.

10. The method of claim 1, wherein the spacer member comprises one or more complementary features captured by sidewalls of the first spacer channel and sidewalls of the second spacer channel when the spacer member is inserted in the first spacer channel and the second spacer channel.

11. The method of claim 1, wherein the end plate and spacer member are an integrated piece.

12. The method of claim 1, wherein the end plate defines a set of fastener holes including at least one fastener hole positioned to be proximate to a first of the adjacent vertebrae and a second fastener hole positioned to be proximate to a second of the adjacent vertebrae.

13. The method of 1, wherein at least a portion of the spinal implant is formed of a biocompatible material.

14. The method of 1, wherein a first implant plate outer surface and a second implant plate outer surface are configured to promote osseointegration.

15. The method of claim 1, wherein the first implant plate and second implant plate are shaped to substantially conform to the shape of the adjacent vertebrae.

16. The method of claim 1, wherein a first implant plate outer surface is sloped and a second implant plate outer surface is sloped.

17. The method of 1, wherein the first implant plate and the second implant plate comprise holes to promote bone growth.

* * * * *